United States Patent [19]

Finch et al.

[11] Patent Number: 5,580,895
[45] Date of Patent: Dec. 3, 1996

[54] 1,5-BENZODIAZEPINE DERIVATIVES

[75] Inventors: Harry Finch, Ware, Great Britain; David G. Trist, Verona, Italy; Giorgio Tarzia, Verona, Italy; Aldo Feriani, Verona, Italy

[73] Assignee: Glaxo SpA, Verona, Italy

[21] Appl. No.: 256,359

[22] PCT Filed: Jan. 15, 1993

[86] PCT No.: PCT/EP93/00098

§ 371 Date: Jul. 20, 1994

§ 102(e) Date: Jul. 20, 1994

[87] PCT Pub. No.: WO93/14074

PCT Pub. Date: Jul. 22, 1993

[30] Foreign Application Priority Data

Jan. 21, 1992 [GB] United Kingdom ............... 9201180

[51] Int. Cl.$^6$ .................. A61K 31/55; A61K 37/02; C07D 243/12; C07D 403/12

[52] U.S. Cl. ............................. 514/221; 540/518

[58] Field of Search .................. 540/518; 514/221

[56] References Cited

FOREIGN PATENT DOCUMENTS 0376849  7/1990  European Pat. Off. ............. 514/221

Primary Examiner—Robert T. Bond
Attorney, Agent, or Firm—Bacon & Thomas

[57] ABSTRACT

The present invention relates to compounds of formula (I) which are antagonists of gastrin and CCK-B receptors. The compounds of formula (I) are 1,5-benzodiazepine derivatives.

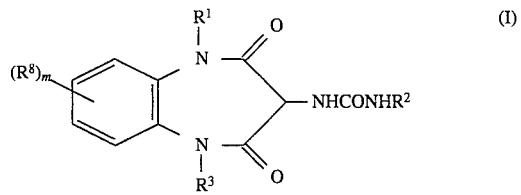

14 Claims, No Drawings

1,5-BENZODIAZEPINE DERIVATIVES

This invention relates to novel 1,5-benzodiazepine derivatives, to processes for their preparation, to pharmaceutical compositions containing them and to their use in medicine.

In particular the invention relates to compounds which are potent and specific antagonists of gastrin and/or cholecystokinin (CCK).

Thus, the invention provides compounds of general formula (I)

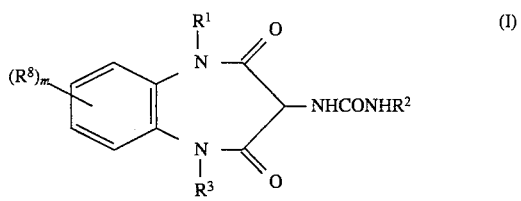

wherein
- $R^1$ represents a phenyl, $C_{3-7}$cycloalkyl, $C_{7-11}$bridgedeycloalkyl or $C_{1-6}$alkyl group which alkyl group may be substituted by a hydroxy, phenyl, $C_{1-6}$alkoxycarbonyl, $C_{3-7}$cycloalkyl, or $C_{7-11}$bridgedcycloalkyl group;
- $R^2$ represents a substituted or unsubstituted phenyl group (wherein the substituents may be 1 or 2 of halo, $C_{1-4}$alkyl, nitro, cyano, trifluoromethyl, trifluoromethoxy, $C_{1-4}$alkylthio or $(CH_2)_n R^4$ wherein $R^4$ is hydroxy, $C_{1-4}$alkoxy, $CO_2R^5$ or $NR^6R^7$.
- $R^3$ is phenyl optionally substituted by one or two halogen atoms;
- $R^5$ represents hydrogen or a $C_{1-4}$alkyl group;
- $R^6$ and $R^7$ independently represent hydrogen or a $C_{1-4}$alkyl group.
- $R^8$ represents hydrogen or a halogen atom; m is zero, 1 or 2;
- n is zero or 1; and pharmaceutically acceptable salts and solvates thereof.

It will be appreciated that compounds of formula (I) possess at least one asymmetric carbon atom (namely the carbon atom occupying the 3-position of the diazepine ring) and the compounds of the invention thus include all stereoisomers and mixtures thereof including the racemates.

In the compounds of formula (I) 'alkyl' when used as a substituent or part of a substituent group means that the group may be straight or branched. Thus, $C_{1-6}$ alkyl includes methyl, ethyl, n-propyl, isopropyl, n-butyl, isobutyl or tertbutyl, n-pentyl, isopentyl neopentyl, n-hexyl, isohexyl, 1,3-dimethylbutyl, 3,3-dimethylbutyl, 2,3-dimethylbutyl.

For the group $R^1$ the term $C_{3-7}$cycloalkyl as a group or part of a group refers to a monocyclic alkyl group such as cyclopropyl, cylobutyl, cyclopentyl, cyclohexyl or cycloheptyl. The term $C_{7-11}$ bridged cycloalkyl refers to groups such adamantyl, norbornanyl or norbornenyl.

For the groups $R^5$ $R^6$ and $R^7$ the term $C_{1-4}$alkyl includes 3–cycloalkyl (e.g. cyclopropyl or cyclobutyl) as well as straight or branched chain alkyl groups as defined above.

Halogen in the definition of compounds of formula (I) may represent a fluoro, chloro, bromo or iodo substituent.

When $R^2$ is a phenyl group substituted by a single substituent this may be in the ortho, para or more preferably in the meta position.

When $R^8$ is halogen this is preferably chlorine or fluorine.

When m is 1 or 2 the halogen atom(s) e.g. chlorine or fluorine are preferably in the 7 and/or 8 positions.

The compounds of formula (I) posses at least one asymmetric carbon atom (namely the carbon atom occupying the 3-position of the diazeine ring) and particularly preferred compounds of the invention or those having the relative stereochemistry shown in formula (1a)

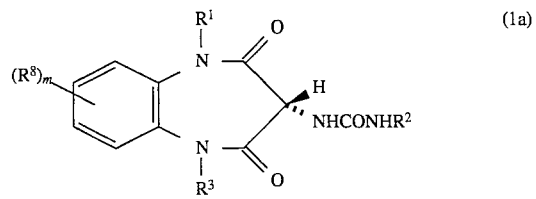

wherein the solid wedge bond indicates the group is above the plane of the diazepine ring and the broken bond indicates the group is below the plane of the diazepine ring.

When $R^1$ represents an alkyl group substituted by a hydroxyl group this is preferably a $C_{3-6}$alkyl group substituted by hydroxy. Examples of such groups include 2-hydroxypropyl, 2-hydroxy-3-methylbutyl and 2-hydroxy-3,3-dimethylbutyl of which 2-hydroxy-3-methylbutyl, and 2-hydroxy-3,3-dimethylbutyl are particularly preferred.

When $R^1$ represent an alkyl group substituted by a $C_{3-7}$cycloalkyl group this is preferably a $C_{2-3}$alkyl group such as ethyl or 1-methylethyl, substituted by a $C_{3-7}$cycloalkyl group such as cyclopentyl.

When $R^1$ is a bridged $C_{7-11}$cycloalkyl group this may be for example an adamantyl group such as 1-adamantyl or 2-adamantyl group or a 2-norbornanyl group.

When $R^1$ is an alkyl group substituted by a bridged $C_{7-11}$cycloalkyl group this is preferably an ethyl group or more especially a methyl group substituted by a bridged $C_{7-11}$cycloalkyl group. Examples of suitable briged cycloalkyl groups include adamantyl such as 1-adamantyl or 2-adamantyl, 2-norbornanyl or 5-norbornenyl. Most preferably $R^1$ represents 1-adamantylmethyl.

When $R^1$ is alkyl substituted by phenyl this may be for example benzyl or phenethyl.

When $R^1$ is alkyl substituted by alkoxycarbonyl this is preferably methyl substituted by alkoxycarbonyl such methoxycarbonyl or as t-butoxycarbonyl.

A preferred class of compounds of formula (I) is that in which $R^1$ represents a phenyl, adamantyl, norbornanyl, phenethyl, $C_{4-6}$alkyl e.g. n-butyl, 3-methyl butyl, 3,3-dimethyl butyl, 1,3-dimethylbutyl, 2,3-dimethylbutyl, $C_{3-6}$hydroxy alkyl e.g. 2-hydroxypropyl, 2-hydroxy-3-methylbutyl, 2-hydroxy-3,3-dimethylbutyl, $C_{1-2}$alkyl substituted by a bridged $C_{7-10}$cycloalkyl group e.g. 2-norbornanylmethyl, 5-norbornanylmethyl, 2-adamantylmethyl, 2-adamantylethyl, 2-(1-adamantyl)ethyl, 1-adamantylmethyl, alkoxycarbonylalkyl, e.g. methoxycarbonylmethyl or t-butyoxycarbonylmethyl, or 2-cyclopentylethyl.

A particularly preferred class of compounds of formula (I) is that in which $R^1$ is 3-methylbutyl, 3,3-dimethylbutyl, 2-hydroxy-3-methylbutyl, 2-hydroxy-3,3-dimethylbutyl, 2-cylopentylethyl, 5-norbornanylmethyl or 1-adamantylmethyl.

A further preferred class of compounds of formula (I) is that in which $R^2$ represents phenyl optionally substituted by bromine, chlorine, fluorine, methyl, methoxy. methylthio, trifluoromethoxy, cyano, dimethylamino or $(CH_2)_nCO_2R^5$ wherein $R^5$is hydrogen or ethyl. Most preferably $R^2$ represents phenyl optionally substituted by methoxy, dimethylamino, cyano, methylthio, $CO_2H$ or $CO_2C_2H_5$.

A further preferred class of compounds of formula (I) is that in which $R^3$ represents phenyl or phenyl mono- or di-substituted by fluorine, preferably in the ortho and/or para position(s). Preferably $R^3$represents unsubstituted phenyl or orthofluorophenyl.

A preferred group of compounds of formula (I) those wherein $R^1$ represents $C_{4-6}$alkyl such as 3-methylbutyl, 3,3-dimethylbutyl, 2-hydroxy-3-methylbutyl, 2-hydroxy-3,3-dimethylbutyl 2-cyclopentylethyl, 5-norbornenylmethyl or 1 adamantylmethyl; $R^2$ represents phenyl or phenyl substituted by methoxy, cyano, nitro, carboxyl, ethoxycarbonyl, methylthio, or dimethylamino and preferably the substituent is in the meta 1-position;

$R^1$ represents phenyl or ortho fluorophenyl; $R^8$ represents hydrogen, chlorine of fluorine; and enantiomers and salts thereof.

A particularly preferred group of compounds of formula (I) are those wherein $R^1$ is 3-methylbutyl; $R^2$ is phenyl optionally substituted in the meta position by methylthio or dimethylamino group; $R^3$ is phenyl or ortho fluorophenyl; $R_8$ is hydrogen or chlorine or fluorine and m is zero, 1 or 2.

A further particularly preferred group of compounds of formula (I) are those wherein $R^1$ represents 1-adamantylmethyl $R^2$ is phenyl optionally substituted in the meta position by a methyl, methoxy, methylthio, nitro, dimethylamino, ethoxycarbonyl or carboxyl group; $R^3$ is phenyl and $R^8$ is hydrogen. Within this group especially preferred compounds are those wherein $R^2$ is phenyl optionally substituted by dimethylamino, ethoxycarbonyl or carboxyl group Preferred compounds according to the invention include:

N-phenyl-N'-[2,3,4,5-tetrahydro-2,4-dioxo-1-(3-methylbutyl)-5-phenyl-1H-1,5-benzodiazepin-3-yl]urea;

N-[1-(3,3-Dimethyl-2-hydroxybut-1-yl)-2,4-dioxo-5-(2-fluorophenyl)-3,4,5-tetrahydro-1H-1,5-benzodiazepin-3-yl]-N'-phenylurea N-phenyl-N'-[2,3,4,5-tetrahydro-2,4-dioxo-1-(3,3-dimethylbutyl)-5-phenyl-1H-1,5-benzodiazepin-3-yl]urea;

N-phenyl-N'-[2,3,4,5-tetrahydro-2,4-dioxo-1-(1-adamantylmethyl)-5-phenyl-1H-1,5-benzodiazepin-3-yl]urea;

N-[2,4-Dioxo-1-(2-hydroxy-3-methylbutyl)-5-phenyl-2,3,4,5-tetrahydro-1H-1,5-benzodiazepin-3-yl]-N'-phenylurea N-(3-dimethylaminophenyl)-N'-[2,3,4,5,-tetrahydro-2,4-dioxo-1-(3-methylbutyl)-5-(2-fluorophenyl)-1H-1,5-benzodiazepin-3-yl]urea;

N-[1-(1-Adamantylmethyl)-2,4-dioxo-5-phenyl-2,3,4,5-tetrahydro-1H-1,5-benzodiazepin-3-yl]-N'-(3-ethoxycarbonylphenyl)urea N-[1-(1-Adamantylmethyl)-2,4-dioxo-5-phenyl-2,3,4,5-tetrahydro-1H-1,5-benzodiazepin-3-yl]-N'-[3-(N,N-dimethylamino)phenyl]urea N-[1-(1-Adamantylmethyl)-2,4-dioxo-5-phenyl-2,3,4,5-tetrahydro-1H-1,5-benzodiazepin-3-yl]-N'-(3-carboxyphenyl)urea N-[1-(Adamantane-1-methyl)-2,4-dioxo-7-fluoro-5-(4-fluorophenyl)-2,3,4,5-tetrahydro-1H-1,5benzodiazepin-3-yl]-N'(3-dimethylamino)phenylurea and (+) enantiomers and salts thereof.

Particularly preferred compounds according to the invention include:

N-phenyl-N'-[2,3,4, 5-tetrahydro-2,4-dioxo-1-(1-adamantylmethyl)-5-phenyl-1H-1,5-benzodiazepin-3-yl]urea;

N-[1-(1-Adamantylmethyl)-2,4-dioxo-5-phenyl-2,3,4,5-tetrahydro-1H-1,5-benzodiazepin-3-yl]-N'-(3-carboxyphenyl)urea N-phenyl-N'-[2,3,4,5-tetrahydro-2,4-dioxo-1-(3-methylbutyl)-5-phenyl-1H-1,5-benzodiazepin-3-yl]urea;

N-(3-dimethylaminophenyl)-N'-[2,3,4,5-tetrahydro-2,4-dioxo-1-(3-methylbutyl)-5-(2-fluorophenyl)-1H-1,5-benzodiazepin-3-yl]urea;

and the (+) enantiomers thereof and salts thereof.

The pharmaceutically acceptable salts of the compounds of formula (I) include conventional salts formed for example from pharmaceutically acceptable inorganic or organic acids as well as quaternary ammonium acid addition salts. Examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

The compounds of formula (I) in which $R^5$ represents hydrogen may form pharmaceutically acceptable salts with suitable cations. Suitable pharmaceutically acceptable cations include alkali metal (e.g. sodium or potassium) and alkaline earth metal (e.g. calcium or magnesium) cations.

References hereinafter to a compound according to the invention includes both compounds of formula (I) and their pharmaceutically acceptable salts and solvates.

The compounds of the invention are potent and specific antagonists of gastrin and/or CCK. The compounds of the invention have been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

The compounds of the invention have also been shown to be antagonists of gastrin as demonstrated by their ability to inhibit pentagastrin-stimulated acid secretion from rat isolated gastric mucosa using the procedure described by J. J. Reeves and R. Stables in *Br. J. Pharmac.*, 1985, 86, p.677–684.

Compounds of the invention have also been found to have a significantly weaker activity at CCK-A receptors compared with their activity at gastrin and/or CCK-B receptors, as demonstrated by their ability to inhibit the contractile activity of CCK-8 in guinea-pig siolated ileum longitudinal muscle-myenteric plexus.

The preparation and use of guinea-pig isolated ileum longitudinal muscle-myenteric plexus has been described by K-H Buchheit et al in Nauyn-Schmeideberg's Arch. Pharmacol, (1985), 329, p36–41 and by V. L. Lucaites et al (1991) in J. Pharmacol. Exp. Ther., 256, 695–703.

The greater affinity of the compounds of the invention for the CCK-B receptor over the CCK-A receptor has also been established using the CCK receptor binding assays described by G. Dal Fornos et al., J. Pharmcol. Exp & Ther. 261, 1056–1063, 1992.

The compounds of the invention are therefore useful for the treatment and/or prevention of disorders in mammals, especially humans, where modification of the effects of gastrin or CCK is of therapeutic benefit. Thus the compounds of the invention are useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), tardive dyskinesia, depression, Parkinson's disease or psychosis. The compounds of the invention are also useful for the treatment of gastrointestinal disorders especially those where there is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. They may also be useful for the treatment of dependency on drugs or substances of abuse and withdrawal, Gilles de la Tourette syndrome, or dysfunction of appetite regulatory systems; as well as the treatment of certain tumours of the lower oesophagus, stomach, intestines and colon. Compounds of the invention are also useful for directly inducing analgesia, or enhancing opiate or non-opiate mediated analgesia, as well as anaesthesia or loss of the sensation of pain.

Compounds of the invention have also been found to exhibit anxiolytic activity in conventional pharmacological tests. For example in mice in the black-white box test and in the rat social interaction model.

The invention therefore provides a compound of formula (I) or a pharmaceutically acceptable salt or solvate thereof for use in therapy, in particular in human medicine.

According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective mount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 0.01–2000mg per day e.g 0.01–500 mg per day.

The desired dose may conveniently be presented in a single dose or as divided doses administered at appropriate intervals, for example as two, three, four or more sub-doses per day.

Because the compounds of the invention antagonise the function of CCK in animals, they may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, accacia, gelatin, sorbitol, tragacanth, hydroxypropyl cellulose, mucilage of starch or polyvinylpyrrolidone; fillers, for example, lactose, sugar, microcrystalline cellulose, maize-starch, calcium phosphate or sorbitol; lubricants, for example, hydrogenated vegetable oils, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in prefilled syringes, vials and ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form which may be obtained by freeze drying for constitution with a suitable vehicle, e.g. sterile, pyrogen-free water, before use.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R^1$–$R^8$ are as defined for the compounds of formula (I) unless otherwise stated.

According to a first general process (A) compounds of formula (I) may be prepared by reacting a compound of formula (II) in which X represents the group —N=C=O, or NHCOR$^9$ wherein R$^9$ is an optionally substituted phenoxy group or a 1-imidazole group.

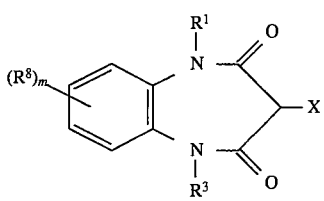

with an amine of formula (III)

$H_2NR^2$ (III)

optionally in the presence of a base such as a tertiary amine (e.g. triethylamine). The reaction conveniently takes place in a suitable solvent such as a halogenated hydrocarbon (e.g. dichloromethane) or an ether (e.g. tetrahydrofuran) or an amide e.g. N,N-dimethylformanide optionally at a temperature ranging from room temperature to the reflux temperature of the solvent.

In a particular aspect of the process (A) when X is the group $NHCOR^9$ and $R^9$ is a 1-imidazole group, the imidazolide (II) may be formed in situ in which case the amine of formula (III) will be mixed with a compound of formula (IV)

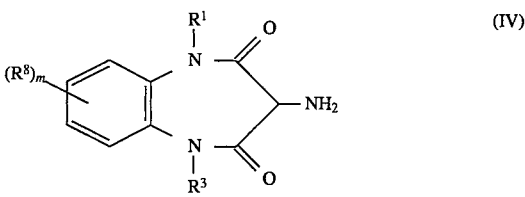

in the presence of carbonyldiimidazole under the aforementioned conditions.

For process A when X is the group $NHCOR^9$ and $R^9$ is optionally substituted phenoxy group the reaction with the primary amine (III) is preferably carried out in the presence of a base such as a tertiary amine e.g. triethylamine.

For process A when X is the isocyanate group —N=C=O the reaction with the primary amine (III) is preferably carried out in an aprotic solvent such as a halohydrocarbon e.g. methylene chloride. Conveniently the isocyante is generated in situ prior to the addition of the primary amine (III).

The compounds of formula (II) wherein $R^9$ is an optionally substituted phenoxy group may be prepared from the primary amine (IV) by reaction with the corresponding optionally substituted phenyl chloroformate in the presence of a base such as pyridine. The reaction may be carried out in a solvent such as a halohydrocabon e.g. dichloromethane and at a temperature from 0°–50°.

Compounds of formula (II) wherein $R^9$ is a 1-imidazole group may be prepared by reacting a compound of formula (IV) with carbonyldiimidazole in the presence of a suitable solvent such as a halogenated hydrocarbon (e.g. dichloromethane) or an ether (e.g. tetrahydrofuran) at a temperature ranging from 0° to 80° (conveniently at room temperature).

Compounds of formula (II) wherein X is the isocyanate grouping —N=C=O may be prepared from the primary amine (IV) by reaction with phosgene ($COCl_2$) in a suitable solvent such as methylene chloride.

According to a further general process (B) compounds of formula (I) may be prepared by reacting a compound of formula (IV) with an isocyanate of formula (V)

$O=C=N-R^2$ (V)

or a carbamoyl chloride of formula (VI)

$ClC(O)NHR^2$ (VI)

The reaction conveniently takes place in the presence of a suitable solvent such as a halohydrocarbon (e.g. dichloromethane), an ether (e.g tetrahydrofuran) or a nitrile (e.g. acetonitrile) or a mixture thereof at a temperature in the range of 0° C. to 80° C.

Compounds of formula (IV) may be prepared by reduction of compounds of formula (VII)

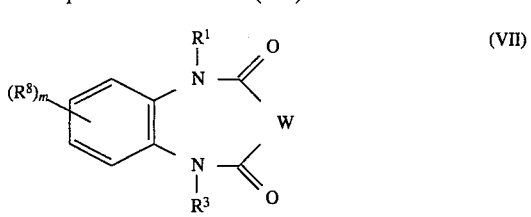

wherein W is $CH-N_3$ or $C=N-NHPh$.

Compounds of formula (VII) wherein W is $CH-N_3$ may be reduced to a compound of formula (IV) by hydrogenation in the presence of a suitable catalyst such as palladium, on a support such as carbon or calcium carbonate, or platinum (IV) oxide. The reaction conveniently takes place in the presence of a solvent such as an alkanol (e.g. ethanol) an ester (e.g. ethyl acetate) or acetic acid.

Compounds of formula (VII) wherein W is $C=N-NHPh$ may be reduced to a compound of formula (IV) by reaction with zinc and acetic acid. This reaction may be carded out a temperature with the range 0°–50°.

Compounds of formula (VII) wherein W is $CHN_3$ may be prepared from a compound of formula (VII) wherein W is $CH_2$ by treatment with a strong base such as sodium hydride or potassium tert-butoxide followed by tri-isopropyl benzenesulphonyl azide. The reaction conveniently takes place in a solvent such as an ether (e.g. tetrahydrofuran) at a temperature in the range of −780° to 20°.

Compounds of formula (VII) in which W is $C=NNHPh$ may be prepared by reaction of the ortho-phenylenediamine (VIII) with the diacid chloride (IX), in a suitable solvent such as an ether e.g. tetrahydorfuran

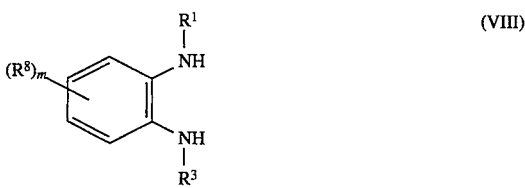

Compounds of formula (VII) wherein W is $CH_2$ prepared by reaction of the corresponding compound (X)

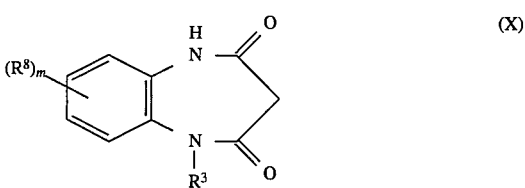

with a compound $R^1Y$ where Y is halogen (e.g. a chlorine or bromine atom) or a mesylate group under strongly basic conditions. Thus the reaction may conveniently be carried out by pretreating the compound of formula (X) with a strong base such as sodium hydride in a suitable aprotic solvent such as an amide (e.g. N,N-dimethylformamide) at a temperature ranging from 0° to reflux.

In the above described reaction scheme when the group $R^1$ contains an hydroxyl group then this may be present in a protected form e.g. as an ether such as an arylmethyl ether e.g. a benzyl ether.

Compounds of formula (VIII) are either known compounds or may be prepared by analogous methods. Thus for example a compound of formula (VIII) may be prepared by alkylation of the amine (XI).

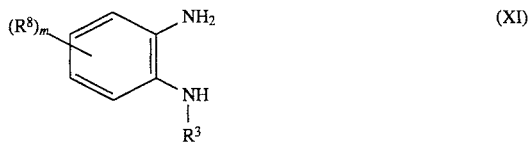

Thus the amine (XI) may be reacted with the compound $R^1Y$, in which Y is chlorine or bromine, optionally in the presence of sodium iodide in a solvent such as N,N-dimethylformamide.

Compounds of formula (VIII) wherein $R^1$ represents the group $-CH_2-CH(OH)R^1_a$ where $R^1_a$ is a $C_{1-4}$ alkyl group may be prepared by reaction of compound (XI) with the epoxide (XII) in a solvent such as an alkanol e.g. ethanol and in the presence of an acid catalyst such as p-toluene sulphonic acid.

Compounds of formula (VIII) where in $R^1$ is an optionally substituted alkyl group. May also be prepared from compound (XI) by reaction with a suitable aldehyde or ketone with concomitant or subsequent reduction of the reaction product. Thus for example a compound formula (VIII) wherein $R^1$ is 1,3-dimethylbutyl may be prepared from compound (XII) by reaction with methylisobutyl ketone followed by reaction with sodium borohydride.

In general, the compounds of formula (III), V and (VI) are either known compounds or may be prepared according to methods used for the preparation of known compounds, According to a further process (C) a compound of formula (I) may be converted into another compound of formula (I) using conventional techniques.

Thus compounds of formula (I) wherein $R^2$ is a phenyl group substituted by a carboxyl group may be prepared by hydrolysis of the corresponding compound of formula (I) wherein $R^2$ is a phenyl group substituted by an alkoxycabonyl group.

In the processes described above the group $R^1$ and $R^2$ in the intermediates II, III, V and VI may be a group as defined in formula (I) or a group convertible thereto.

The foregoing series of reactions involve a number of alternative pathways which may start with the 1,5-benzodiazepine of formula (X) as defined above. Thus according to a further general process (D) a compound of formula (I) may be prepared by reacting a compound of formula (X) in one or more stages with reagents serving to introduce the groups $R^1$ and $NHCONHR^2$.

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as chiral HPLC. Alternatively the required enantiomer may be prepared by the corresponding enantiomeric amine of formula (IV) using any of the processes described above for preparing compounds of formula (I) from the amine (IV). The enantiomers of the amine (IV) may be prepared from the racemic amine (IV) using conventional procedures such as salt formation with a suitably optically active acid such as R-camphorsulphonic acid.

The following examples, which are non-limiting, illustrate the invention.

In the Preparations and Examples, unless otherwise stated: Melting points (m.p.) were determined on a Buchi m.p. apparatus and are uncorrected. All temperatures refer to 0 C. Infrared spectra were measured in chloroform-$d_1$ solutions on a FT-IR instrument. Proton Magnetic Resonance (1H-NMR) spectra were recorded at 300 MHz as solutions in chloroform-$d_1$. Chemical shifts are reported in ppm downfield (δ) from Me4Si as an internal standard, and are assigned as singlets (s), doublets (d), doublet of doublets (dd) or multiplets (m). Column chromatography was carried out over silica gel (Merck AG Darmstadt, Germany). Solutions were dried over anhydrous sodium sulphate. "Petrol" refers to petroleum ether, b.p.40°–60° C. Dichloromethane was redistilled over calcium hydride; tetrahydrofuran was redistilled over sodium; ethyl ether was redistilled over sodium and ethyl acetate was dried over activated molecular sieves. The following abbreviations are used in the text. EA=ethyl acetate, CH=cyclohexane, P=petroleum ether 40°–60° C., THF=tetrahydrofuran, DCM=dichloromethane, EE=ethyl ether, DMF=N,N-dimethylformamide. Tlc refers to thin layer chromatography on silica plates. All the compounds are intended as racemic mixtures unless otherwise indicated.

Intermediate 1

2-Fluoro-2'-(3-methylbut-1-yl)amino-diphenylamine

1-Bromo-3-methylbutane (4.33 ml) was added to a solution of the 2-amino-2'-fluorodiphenylamino (7.0 g) and sodium iodide (5.24 g) in dimethylformamide (250 ml) under a nitrogen atmosphere. The solution was stirred at 120° for 8 h, then cooled to room temperature, diluted with water (300 ml) and extracted with diethyl ether (2×250 ml). The combined organic extracts were washed with brine (300 ml), dried and concentrated in vacuo to an oil, which was purified by flash chromatography (eluting with CH-EA 95:5) to give the title compound as a yellow oil (6.3 g). T.l.c. CH-EA (9:1) Rf 0.75.

Intermediate 2

2,4-Dioxo-5-(2-fluorophenyl)-1-(3-methylbut-1-yl)-3-phenylhydrazono-2,3,4,5-tetrahydro-1H-1,5-benzodiazepine The intermediate 1 (6.3 g) and the 2-phenylhydrazonomalonyldichloride (6.8 g) were each taken up in THF (150 ml) and dropped in a flask containing THF (200 ml) maintained at −5° under a nitrogen atmosphere. After complete addition the solution was allowed to warm to room temperature and then heated to 50° for 2 h. The solution was concentrated in vacuo to an oil, which was purified by flash chromatography (eluting with CH-EA 8:2) to give the title compound as a yellow solid (5.8 g). M.p.104°–105° T.l.c. CH-EA (7:3), Rf 0.59.

Intermediate 3

3-Amino2,4-dioxo-5-(2-fluorophenyl)-1-(3-methylbut-1yl)-2,3,4,5-tetrahydro-1H1,5-benzodiazepine A solution of the intermediate 2 (5.8 g) in glacial acetic acid (50 ml) was added, dropwise, to a suspension of zinc dust (6.37 g) in glacial acetic acid (20 ml) cooled to 0°. The mixture was stirred at 23° for 3 h, then diluted with water (200 ml) and decanted from zinc. Solid sodium carbonate was added until pH=9 and the mixture extracted with ethyl acetate (2×300 ml). The combined organic extracts were washed with brine (300 ml), dried and concentrated in vacuo to an oil which was purified by flash chromatography (eluting in gradient from CH-EA 2:1 to EA) to give the title compound as a white foam (2.8 g). M.p. 125°–6°. T.l.c. DCM-methanol (30:1), Rf 0.38.

Intermediate 4

2-(3,3-Dimethylbut-1-yl)amino-2'-fluoro-diphenylamine

Sodium borohydride (22.7 g) was added portionwise to a mixture of the 2-amino-2'-fluorodiphenylamine (8.0 g), sodium acetate trihydrate (16.33 g) and 3,3-dimethylbutyraldehyde (5 ml) in acetic acid (12.8 ml), water (50 ml) and ethanol (40 ml) cooled to 0°. The solution was stirred at 23° for 30 min., then diluted with ethyl acetate (300 ml). The organic layer was washed with a 10% solution of sodium hydroxide (3×200 ml) and brine (200 ml), dried and concentrated in vacuo to an oil, which was purified by flash chromatography (eluting with CH-EA 9:1) to give the title compound as a yellow oil (7.44 g). T.l.c. CH-EA (9:1), Rf 0.85.

Intermediate 5

1-(3,3-Dimethylbut-1-yl)-2,4-dioxo-5-(2-fluorophenyl)-3-phenylhydrazono-2,3,4,5-tetrahydro-1H-1,5-benzodiazepine The intermediate 4 (7.73 g) and the 2-phenylhydrazonomalonyldichloride (7.97 g) were each taken up in THF (100 ml) and dropped in a flask containing THF (300 ml) maintained at −5° under a nitrogen atmosphere. After complete addition the solution was allowed to warm to room temperature and then heated to 50° for 3 h. The solution was concentrated in vacuo to an oil, which was purified by flash chromatography (eluting with CH-EA 8:2) to give the title compound as yellow solid (1 0.8 g). M.p.112°–114°. T.l.c. CH-EA (8:2), Rf 0.40.

Intermediate 6

3-Amino-1-(3,3-dimethylbut-1-yl)-2,4-dioxo-5-(2-fluorophenyl)-2,3,4,5-tetrahydro-1H-1,5-benzodiazepine A solution of the intermediate 5 (10.1 g) in glacial acetic acid (80 ml) was added, dropwise, to a suspension of zinc dust (10.8 g) in glacial acetic acid (20 ml) cooled to 0°. The mixture was stirred at 23° for 2 h, then diluted with water (200 ml) and decanted from zinc. Solid sodium carbonate was added until pH=9 and the solution then extracted with ethyl acetate (3×250 ml). The combined organic extracts were washed with brine (400 ml), dried and concentrated in vacuo to an oil, which was purified by flash chromatography (eluting in gradient from CH-EA 2:1 to ethyl acetate) to give the title compound as a white foam (5.4 g). M.p. 98°–100°. T.l.c. DCM-methanol (20:0.5), Rf 0.3.

Intermediate 7

2,4-Dioxo-5(2-fluorophenyl)-3-isocyanate-1-(3-methylbut-1-yl)-2,3,4,5-tetrahydro-1H-1,5-benzodiazepine Phosgene in toluene (1.93M solution; 7 ml) was added to a solution of the intermediate 3 (0.2 g) in dichloromethane (3 ml). The resulting solution was stirred at 23° for 5 h, then concentrated in vacuo at 50° for 3 h to give the title compound as a white solid (0.21 g). M.p. 167°–80°.

Intermediate 8

2,4-Dioxo-5-(2-fluorophenyl)-1-(3-methylbut-1-yl)-3-(phenyloxycarbonylamino)-2,3,4,5-tetrahydro-1H-1,5-benzodiazepine Pyridine (0.137 ml) and phenyl chloroformate (0.21 ml) were added to a solution of the intermediate 3 (0.3 g) in dichloromethane (15 ml) under a nitrogen atmosphere. The resulting solution was stirred at 23° for 30 min, then washed with a 1% solution of hydrochloric acid (15 ml), a 5% solution of sodium hydrogen carbonate (15 ml) and brine (20 ml). The organic layer was dried and concentrated in vacuo to a solid which was triturated with ethyl acetate to give the title compound as a white solid (0.3 g). M.p. 226°–7°. T.l.c. CH-EA (1:1), Rf=0.75.

Intermediate 9

1-(3,3-Dimethylbut-1-yl)-2,4-dioxo-5-(2-fluorophenyl)-3-(phenyloxycarbonylamino)-2,3,4,5-tetrahydro-1H-1,5-benzodiazepine Pyridine (0.64 ml) and phenyl chloroformate (1.0 ml) were added to a solution of the intermediate 6 (1.5 g) in dichloromethane (100 ml) under a nitrogen atmosphere. The resulting solution was stirred at 23° for 30 min, then washed with a 1% solution of hydrochloric acid (2×70 ml), a 5% solution of sodium hydrogen carbonate (2×70 ml) and brine (100 ml). The organic layer was dried and concentrated in vacuo to a solid which was triturated with diethyl ether to give the title compound as a white solid (1.4 g). M.p. 199°–200°. T.l.c. CH-EA (1:1), Rf=0.82.

Intermediate 10

2-(3,3-Dimethyl-2-hydroxybut-1-yl)amino-2'-fluorodiphenylamine 1,2-Epoxy-3,3-dimethylbutane (7 ml) was added, portionwise, to a mixture of the 2-amino-2'-fluorodiphenylamine (7.46 g) and p.toluenesulfonic acid (0.6 g) in ethanol (30 ml) heated to 80°. The mixture was stirred at 80° for 19 h, then concentrated in vacuo and partitioned between water (100 ml) and ethyl acetate (150 ml). The organic layer was washed with a 5% solution of sodium hydrogen carbonate (2×100 ml), brine (150 ml), dried and concentrated in vacuo to an oil, which was purified by flash chromatography (eluting with CH-EA 80:20) to give the title compound as a yellow oil (3.21 g). T.l.c. CH-DCM (1:1), Rf 0.25.

Intermediate 11

1-(3,3-Dimethyl-2-hydroxybut-1-yl)-2,4-dioxo-5-(2-fluorophenyl)-3-phenylhydrazono-2,3,4,5-tetrahydro-1H-1,5-benzodiazepine The intermediate 10 (1.8 g) and the 2-phenylhydrazonomalonyldichloride (1.76 g) were each taken up in THF (35 ml) and dropped in a flask containing THF (30 ml) maintained at −15° under a nitrogen atmosphere. After complete addition the solution was allowed to warm to room temperature and then heated to 50° for 3 h. The solution was concentrated in vacuo to an oil, which was purified by flash chromatography (eluting with CH-EA 8:2) to give the title Compound as a yellow solid (2.1 g). M.p.217°–8°. T.l.c. CH-EA (2:1), Rf 0.71.

Intermediate 12

3-Amino-1-(3,3-dimethyl-2-hydroxybut-1-yl)-2,4-dioxo-5-(2-fluorophenyl)-2,3,4,5-tetrahydro-1H-1,5-benzodiazepine Zinc dust (2.17 g) was added portionwise to a solution of the intermediate 11 (2.1 g) in glacial acetic acid (30 ml) previously cooled to 0°. The mixture was stirred at 23° for 20 h, then diluted with water (100 ml) and decanted from zinc. Solid sodium carbonate was added until pH=9, and the mixture was extracted with ethyl acetate (3×100 ml). The combined organic extracts were washed with brine (200 ml), dried and concentrated in vacuo to an oil, which was purified by flash chromatography (eluting with EA) to give the title compound as a white foam (1.09 g). M.p. 104°–5° T.l.c. EA-methanol (20:2), Rf 0.66 and 0.61.

Intermediate 13

3-Amino-1-(3,3-dimethyl-2-hydroxybut-1-yl)-2,4-dioxo-5-(2-fluorophenyl)-2,3,4,5-tetrahydro-1H-1,5-benzodiazepine (diastereomer I: 13a and diastereomer II; 13b)

The diastereomeric mixture, intermediate 12 was separated by preparative HPLC (Column Spherisorb 5uCN 25×0.46 cm)eluting with hexanedethanol/isopropanol 85:10:5 and isopropylamine 0.05% (flux 2 ml/min, detection UV at 235 nm) to give the title compound 13a (retention time 8.9 min) as a white solid (0.3 g) M.p. 164°–5° T.l.c. EA-methanol (20:2), Rf 0.66. and the title compound 13b (retention time 6 min) as a white foam (0.35 g). T.l.c. EA-methanol (20:2), Rf 0.61.

Intermediate 14

2-(1,3-dimethylbut-1-yl)amino-diphenylamine

Sodium borohydride (0.4 g) was added portionwise to a mixture of 2-amino-diphenylamine (0.5 g), sodium acetate trihydrate (0.5 g) and 4-methyl-2-oxo-pentane (0.25 ml) in acetic acid (1.7 ml), water (5 ml) and ethanol (4 ml) cooled at 0° C. A further amount of sodium borohydride (2.0 g) and of 4-methyl-2-oxo-pentane (3 ml) were added and the solution was stirred at 23° for 30 min., then diluted with ethyl acetate (100 ml) and water (100 ml) . The organic layer was washed with a 10% solution of sodium hydroxide (50 ml) and brine (50 ml), dried and concentrated in vacuo to give an oil, which was purified by flash chromatography (eluting with CH-EA 90:10) to give the title compound as a yellow oil (0.42 g). T.l.c. CH-EA (90:10), Rf 0.79. IR: 3420 (NH),1599, 1514 and 1497 (C═C) cm–1;

Intermediate 15

1-(1,3-Dimethylbut-1-yl)-2,4-dioxo-5-phenyl-3-phenylhydrazono-2,3,4,5-tetrahydro-1H-1,5-benzodiazepine The intermediate 14 (0.42 g), and 2-phenylhydrazonomalonyldichloride (0.46 g) were each taken up in THF (20 ml) and dropped in a flask containing THF (10 ml) maintained at 0° under a nitrogen atmosphere. After complete addition the solution was allowed to warm to 23° and stirred for 20 h. A further amount of 2-phenylhydrazonomalonyldichloride (0.13 g) was added and stirring continued for 1 h at 23° and then at 50° for 90 min. The reaction mixture was diluted with ethyl acetate (200 ml); the organic layer was washed with a 10% solution of sodium hydroxide (60 ml) and brine (2×70 ml), dried and concentrated in vacuo to give an oil, which was purified by flash chromatography (eluting with CH-EA 95:5, increasing polarity to 90:10) to give the title compound as a yellow solid (0.43 g). T.l.c. CH-EA (70:30), Rf 0.73. IR: 1668, 1653 (C═O); 1591 (C═C) cm–1;

Intermediate 16

3-Amino-1-(1,3-dimethylbut-1-yl)-2,4-dioxo-5-phenyl-2,3,4,5-tetrahydro-1H-1,5-benzodiazepine Zinc dust (0.55 g) was added portionwise to a solution of the intermediate 15 (0.42 g) in glacial acetic acid (10 ml) cooled at 0°. The mixture was stirred at 23° for 8 h, then decanted from zinc, diluted with ethyl acetate (50 ml), washed with a 10% solution of sodium hydroxide (60 ml), brine (2×60 ml), dried and concentrated in vacuo to give an oil which was purified by flash chromatography (eluting in gradient from CH-EA 1:1 to DCM-methanol 90:10) to give the title compound as a white foam (0.22 g). T.l.c. DCM-methanol (90:10), Rf 0.53. IR: 3500–3000 (NH2), 1703 and 1672 (C═O), 1593 (C═C) cm–1;

Intermediate 17

2-Amino-5-chloro-diphenylamine

Potassium carbonate (29 g) and sodium hydrosulphite (25.3 g) were added portionwise over 1 hour to a suspension of 5-chloro-2-nitrodiphenylamine (8 g) in 95% ethanol (250 ml) and water (250 ml). The mixture was stirred at 23° for 20 h, then a further amount of sodium hydrosulfite (1 g) was added and stirring continued for 1 h. The reaction mixture was acidified to pH4 with conc. hydrochloric acid and then a 10% solution of sodium hydroxide was added until the pH was 10. The solution was concentrated in vacuo and extracted with ethyl ether (2×250 ml). The combined organic extracts were washed with brine (2×250 ml), dried and concentrated in vacuo to give the crude compound as a yellow solid (7.8 g) which was purified by flash chromatography (eluting with P-EE 1:1) to give the title compound as a yellow foam (4.4 g). T.l.c. CH-EA (1:1), Rf 0.50. IR: 3412 and 3320 (NH), 1592–1589 (C═C) cm–1;

Intermediate 18

5-Chloro-2-(3-methylbut-1-yl)amino-diphenylamine

Sodium borohydride (2 g) was added portionwise to a mixture of the intermediate 17 (2 g), sodium acetate trihydrate (2.28 g) and 3-methylbutyraldehyde (2 ml) in acetic acid (8 ml), water (15 ml) and ethanol (35 ml) cooled to 0° C. The solution was stirred at 23° for 30 min, then diluted with ethyl acetate (200 ml). The organic layer was washed with a 10% solution of potassium carbonate (100 ml) and brine (100 ml), dried and concentrated in vacuo to give an oil, which was purified by flash chromatography (eluting with CH-EA 95:5) to give the title compound as a yellow oil (0.8 g). T.l.c. CH-EA (1:1), Rf 0.72.

Intermediate 19

7Chloro2,4-dioxo-1-(3-methylbut-1-yl)-5-phenyl-3-phenylhydrazono-2,3,4,5-tetrahydro-1H-1,5-benzodiazepine The intermediate 18 (1.15 g) and 2-phenylhydrazonomalonyldichloride (1.17 g) were each taken up in THF (30 ml) and added dropwise in a flask containing THF (10 ml) maintained at 0° under a nitrogen atmosphere. After complete addition the solution was allowed to warm to 23° C., stirred for 30 min., then heated at 60° for 2 h. The solution was diluted with ethyl acetate (150 ml), washed with brine (2×100 ml), dried and concentrated in vacuo to give an oil, which was purified by flash chromatography (eluting with CH-EA 95:5, increasing polarity to 70:30) to give the title compound as a yellow solid (1.12 g). T.l.c. CH-EA (1:1), Rf 0.61. IR: 3452 (NH), 1664 (C=O) cm−1;

Intermediate 20

3-Amino-2,4-dioxo-7-chloro-5-phenyl-1-(3-methylbut-1-yl)-2,3,4,5-tetrahydro-1H-1,5-benzodiazepine A solution of the intermediate 19 (0.6 g) in glacial acetic acid (14 ml) was added, dropwise, to a suspension of zinc dust (0.76 g) in glacial acetic acid (14 ml) cooled at 0°. The mixture was stirred at 23° for 3 h, then decanted from zinc, washed with ethyl acetate (80 ml) and then with 10% sodium hydroxide (100 ml) and brine (70 ml). The combined organic extracts were dried and concentrated in vacuo to give an oil which was purified by flash chromatography (eluting in gradient from CH-EA 1:1 to EA-methanol 27:3) to give the title compound (0.3 g). T.l.c. DCM-methanol (27:3), Rf 0.5.

Intermediate 21

4-Chloro-2-nitrodiphenylamine

A mixture of 4-chloro-2-nitroaniline (5.5 g), bromobenzene (20 ml), potassium carbonate (1.63 g) and copper(I) iodide (0.68 g) was heated to 180° for 36 h. The reaction mixture was cooled to room temperature, then ethyl acetate (200 ml) and water (300 ml) were added; the organic extracts were washed with brine (2×150 ml), dried and concentrated in vacuo to give the crude compound which was purified by flash chromatography (eluting with CH-EA 95:5) to give the title compound (3.67 g). T.l.c. CH-EA (1:1 ), Rf 0.71.

Intermediate 22

2-Amino4-chlorodiphenylamine

Potassium carbonate (13 g) and sodium hydrosulphite (11.4 g) were added portionwise over 3 hour to a suspension of 4-chloro-2-nitrodiphenylamine (3.6 g) in 95% ethanol (100 ml) and water (100 ml). The mixture was stirred at 23° for 20 h. The reaction mixture was then acidified to pH=4 with conc. hydrochloric acid (20 ml); then 10% solution of sodium hydroxide (80 ml) was added until pH=10 and the solution extracted with ethyl acetate (2×150 ml). The combined organic extracts were washed with brine (2×150 ml), dried and concentrated in vacuo to give the crude compound as a yellow solid (7.8 g) which was purified by flash chromatography (eluting with CH-EA 90:10 then 70:30) to give the title compound as a yellow foam (2.37 g). Tlc. CH-EA (1:1), Rf 0.66.

Intermediate 23

4-Chloro-2-(3-methylbut-1-yl)amino-diphenylamine

Bromo 3-methylbutane (0.62 ml) was added to a solution of the intermediate 22 (1.00 g) and sodium iodide (0.7 g) in dimethylformamide (40 ml) under a nitrogen atmosphere. The solution was stirred at 120° for 12 h, then cooled at 23° C., diluted with ethyl acetate (150 ml) and washed with brine (3×100 ml). The combined organic extracts were dried and concentrated in vacuo to give an oil, which was purified by flash chromatography (eluting with CH-EA 95:5) to give the title compound as a yellow oil (0.74 g). T.l.c. CH-EA (1:1), Rf 0.76.

Intermediate 24

8-Chloro-2,4-Dioxo-1-(3-methylbut-1-yl)-5-phenyl-3-phenylhydrazono-2,3,4,5-tetrahydro-1H-1,5-benzodiazepine The intermediate 23 (0.74 g) and the 2-phenylhydrazonomalonyldichloride (0.75 g) were each taken up in THF (15 ml) and dropped in a flask containing THF (20 ml) maintained at 0° under a nitrogen atmosphere. After complete addition, the solution was allowed to warm to 23° C., stirred for 30 min., then heated at 60° for 2 h. The solution was diluted with ethyl acetate (120 ml), washed with brine (2×100 ml), dried and concentrated in vacuo to give an oil, which was purified by flash chromatography (eluting with CH-EA 95:5, increasing polarity to 70:30) to give the title compound as a yellow solid (0.91 g). T.l.c. CH-EA (1:1), Rf 0.68

Intermediate 25

3-Amino-8-chloro-2,4-dioxo-1-(3-methylbut-1-yl)-5-phenyl-2,3,4,5-tetrahydro-1H-1,5-benzodiazepine To the solution of intermediate 24 (0.9 g) in glacial acetic acid (20 ml) at 0°, zinc dust (1.14 g) was added portionwise. The mixture was stirred at 23° for 1 h, then decanted from zinc, washed with ethyl acetate (150 ml) and then with 10% sodium hydroxide (150 ml) and brine (100 ml). The combined organic extracts were dried and concentrated in vacuo to an oil which was purified by flash chromatography (eluting in gradient from CH-EA 1:1 to EA-methanol 27:3) to give the title compound (0.53 g). T.l.c. EA-methanol (27:3), Rf 0.6.

Intermediate 26

4,5-Dichloro-2-nitrodiphenylamine

A mixture of 4,5-dichloro-2-nitroaniline (5.0 g), bromobenzene (16 ml) potassium carbonate (1.17 g) and copper(I) iodide (0.46 g) was heated to 150° for 36 h. The reaction mixture was concentrated in vacuo to give the crude compound which was purified by flash chromatography (eluting with CH-EA 90:10) to give the title compound (4.34 g) T.l.c. CH-EA (1:1), Rf 0.7.

Intermediate 27

2-Amino4,5-dichloro-diphenylamine

Potassium carbonate (13.8 g) and sodium hydrosulfite (12.1 g) were added portionwise over 3 hour to a suspension of 4,5-dichloro-2-nitrodiphenylamine (4.34 g) in 95% ethanol (100 ml) and water (100 ml). The mixture was stirred at 23° for 20 h. The reaction mixture was then acidified to pH=4 with conc. hydrochloric acid (20 ml), then 10% solution of sodium hydroxide (80 ml) was added until pH=10 and the solution extracted with ethyl acetate (2×120 ml). The combined organic extracts were washed with brine (2×100 ml), dried and concentrated in vacuo to give the crude compound which was purified by flash chromatography (eluting with CH-EA 90:10 then 80:20) to give the title compound as a yellow foam (2.15 g). Tlc. CH-EA (1:1), Rf 0.54.

Intermediate 28

4,5-Dichloro-2-(3-methylbut-1-yl)amino-diphenylamine

1-Bromo-3-methylbutane (1.2 ml) was added to a solution of the intermediate 27 (2.15 g) and sodium iodide (1.3 g) in dimethylformamide (70 ml) under a nitrogen atmosphere. The solution was stirred at 120° for 9 h, and at 23° C. for 20 h. A further amount of bromo-3-methylbutane (0.5 ml) was then added and stirring was continued at 120° for 8 h. The reaction mixture was diluted with ethyl acetate (300 ml) and washed with brine (150 ml). The combined organic extracts were dried and concentrated in vacuo to give an oil, which was purified by flash chromatography (eluting with CH-EA 95:5) to give the title compound as a yellow oil (1.72 g). T.l.c. CH-EA (1:1), Rf 0.70.

Intermediate 29

7-8-dichloro-2,4-Dioxo-1-(3-methylbut-1-yl)-5-phenyl-3-phenylhydrazono-2,3,4,5tetrahydro-1H-1,5-benzodiazepine The intermediate 28 (1.72 g) and the 2-phenylhydrazono-malonyldichloride (1.53 g) were each taken up in THF (15 ml) and dropped in a flask containing THF (40 ml) maintained at 0° under a nitrogen atmosphere. After complete addition the solution was allowed to warm at 23° C., stirred for 45 min., then heated at 60° for 1 h and 30 min. The solution was diluted with ethyl acetate (150 ml), washed with brine (2×100 ml), dried and concentrated in vacuo to give an oil, which was purified by flash chromatography (eluting with CH-EA 95:5, increasing polarity to 80:20) to give the title compound as a yellow solid (1.85 g). T.l.c. CH-EA (1:1), Rf 0.66.

Intermediate 30

3-Amino-7-8-dichloro-2,4-dioxo-1-(3-methylbut-1-yl)-5-phenyl-2,3,4,5-tetrahydro-1H-1,5-benzodiazepine To the solution of the intermediate 29 (1.0 g) in glacial acetic acid (15 ml) at 0°, zinc dust (0.65 g) was added portionwise. The mixture was stirred at 23° for 6 h, then decanted from zinc, washed with ethyl acetate (150 ml) and then with 10% sodium hydroxide (150 ml) and brine (100 ml). The combined organic extracts were dried and concentrated in vacuo to give an oil which was purified by flash chromatography (eluting in gradient from CH-EA 1:1 to EA-methanol 80:20) to give the title compound (0.44 g). T.l.c. EA-methanol (27:3), Rf 0.59.

Intermediate 31

4-Fluoro-2-nitrodiphenylamine

A mixture of 4-Fluoro-2-nitroaniline (5.0 g), bromobenzene (20 ml), potassium carbonate (1.54 g) and copper(I) iodide (0.6 1 g) was heated to 150° for 30 h. The reaction mixture was cooled at 23° C., then ethyl acetate (200 ml ) was added; the organic extracts were washed with brine (100 ml), dried and evaporated in vacuo to give the crude compound which was purified by flash chromatography (eluting with CH-EA 95:5) to give the title compound (2.4 g) T.l.c. CH-EA (1:1), Rf 0.68.

Intermediate 32

2-amino-4-Fluoro-diphenylamine

Potassium carbonate (9.3 g) and sodium hydrosulfite (8.2 g) were added portionwise over 3 hour to a suspension of 4-fluoro-2-nitrodiphenylamine (2.4 g) in 95% ethanol (70 ml) and water (70 ml). The mixture was stirred at 23° for 20 h. The reaction mixture was the n acidified to pH=4 with conc. hydrochloric acid (15 ml), then 10% solution of sodium hydroxide (50 ml) was added until pH=10, and the concentrated solution extracted with ethyl acetate (2×100 ml). The combined organic extracts were washed with brine (2×80 ml), dried and concentrated in vacuo to give the crude compound which was purified by flash chromatography (eluting with CH-EA 90:10 then 80:20) to give the title compound as a yellow foam (1.44 g). T.l.c. CH-EA (1:1), Rf 0.72.

Intermediate 33

4-Fluoro-2-(3-methylbut-1-yl)amino-diphenylamine

1-Bromo 3-methylbutane (1.0 ml) was added to a solution of the intermediate 32 (1.44 g) and sodium iodide (1.1 g) in dimethylformamide (60 ml) under a nitrogen atmosphere. The solution was stirred at 120° for 9 h; the reaction mixture was diluted with ethyl acetate (300 ml) and washed with brine (3×150 ml). The combined organic extracts were dried and concentrated in vacuo to give an oil, which was purified by flash chromatography (eluting with CH-EA 95:5) to give the title compound as a yellow oil (0.96 g). T.l.c. CH-EA (1:1), Rf 0.74.

Intermediate 34

2,4-Dioxo-8-fluoro-1-(3-methylbut-1-yl)-5-phenyl-3-phenylhydrazon-2,3,4,5-tetrahydro-1H-1,5-benzodiazepine The intermediate 33 (0.96 g) and 2-phenylhydrazonomalonyldichloride (1.01 g) were each taken up in THF (15 ml) and dropped in a flask containing THF (40 ml) maintained at –0° under a nitrogen atmosphere. After complete addition the solution was allowed to warm at 23° C., stirred for 30 min., then heated at 60° for 2 h. The solution was diluted with ethyl acetate (120 ml), washed with brine (2×100 ml), dried and concentrated in vacuo to give an oil, which was purified by flash chromatography (eluting with CH-EA 95:5, increasing polarity to 80:20) to give the title compound as a yellow solid (1.3 g). T.l.c. CH-EA (1:1), Rf 0.74.

Intermediate 35

3-Amino-2,4-dioxo-8-Fluorol-(3-methylbut-1-yl)-5-phenyl-2,3,4,5-tetrahydro-1H-1,5-benzodiazepine To the solution of the intermediate 34 (1.3 g) in glacial acetic acid (20 ml) at 0°, zinc dust (1.2 g) was added portionwise. The mixture was stirred at 23° for 1 h, then decanted from. zinc, washed with ethyl acetate (150 ml) and then with 10% sodium hydroxide (150 ml) and brine (100 ml). The combined organic extracts were dried and concentrated in vacuo to give an oil which was purified by flash chromatography (eluting in gradient from CH-EA 1:1 to EA-methanol 80:20) to give the title compound (0.72 g). T.l.c. EA-methanol (27:3), Rf 0.47.

Intermediate 36

2,4-Dioxo-5-phenyl-1-(2-phenylethyl)-2,3,4,5-tetrahydro-1H-1,5-benzodiazepine Sodium hydride 80% dispersion in oil (0.13 g) was added portionwise to a solution of the 2,4-dioxo-5-phenyl-2,3,4,5-tetrahydro-1H-1,5-benzodiazepine (compound a) (1 g) in DMF (18 ml) previously cooled at 0°. The reaction was stirred for 20 min at 0°, then a solution of 2-phenylethyl bromide (0.85 ml) in DMF (2 ml) was added dropwise, the mixture was stirred at 23° for 15 h, then diluted with EA (80 ml) and washed with brine (3×100 ml), dried and concentrated "in vacuo". The crude product was purified by flash chromatography (eluting with CH-EA 1:1) to give the title compound as a white powder (0.85 g). T.l.c. CH-EA (1:1), $R_f$=0.27.

Intermediate 37

3-Azido-2,4-dioxo-5-phenyl-1-(2-phenylethyl)-2,3,4,5-tetrahydro-1H-1,5-benzodiazepine A solution of the intermediate 36 (0.85 g) in THF (20 ml), cooled to –700, was added dropwise to a solution of potassium tert-butoxide (0.3 g) in THF (10 ml) cooled to –700, under a nitrogen atmosphere. The mixture was stirred for 20 min at –700, then a solution of 2,4,6-triisopropylbenzenesulphonyl azide (0.96 g) in THF (15 ml), previously cooled to –70° and acetic acid (0.14 ml) were added. The reaction mixture was allowed to stand at 23° and stirred for 1.5 h, then more acetic acid (0.14 ml) was added and the mixture was stirred for 2 h. Ethyl acetate (150 ml) was added and the solution was washed with a saturated solution of sodium hydrogen carbonate (100 ml) and brine (3×100 ml), dried and concentrated "in vacuo". The crude product was purified by flash chromatography (eluting with CH-EA 90:10) to give the title compound as a white foam (0.38 g). T.l.c. CH-EA(1:1), $R_f$=0.57.

Intermediate 38

3-Amino-2,4-dioxo-5-phenyl-1-(2-phenylethyl)-2,3,4,5-tetrahydro-1H-1,5-benzodiazepine A solution of the intermediate 37 (0.38 g) in ethanol (15 ml) and ethyl acetate (15 ml) was stirred under hydrogen, at 1 atm., in presence of 5% Pd/CaCO$_3$ (0.25 g), at 23°, for 3 h. The catalyst was filtered off on a pad of celite, washing with dichloromethane (25 ml) and ethanol (25 ml) and the organic layer was concentrated "in vacuo". The crude product was purified by flash chromatography (eluting with DCM-ethanol 90:10) to give the title compound as a white foam (0.3 g). T.l.c. DCM-ethanol (90:10), $R_f$=0.1.

Intermediate 39

1-(1-Adamantyl)methyl-2,4-dioxo-5-phenyl-2,3,4,5-tetrahydro-1H-1,5-benzodiazepine Sodium hydride 80% dispersion in oil (0.07 g) was added portionwise to a solution of the compound (a) (0.5 g) in DMF (50 ml). The reaction mixture was stirred for 30 min, then a solution of 1-adamantylmethyl methanesulfonate (0.537 g) in DMF (3 ml) was added. The reaction mixture was stirred at 120° for 7 h and at 23° for 15 h, then concentrated. The residue was diluted with ethyl acetate (100 ml) washed with brine (2×30 ml) and water (50 ml), dried and concentrated "in vacuo". The crude product was purified by flash chromatography (eluting with CH-EA 1:1) to give the title compound as a white foam (0.15 g). T.l.c. CH-EA (1:1), $R_f$=0.42.

Intermediate 40

1-(1-Adamantyl)methyl-1-(2-phenylethyl)-3-azido2,4-dioxo-5-phenyl-2,3,4,5-tetrahydro-1H-1,5-benzodiazepine A solution of potassium tert-butoxide (0.146 g) in THF (7 ml) was added dropwise to a solution of the intermediate 39 (0.4 g) in THF (15 ml), cooled to –70°, under a nitrogen atmosphere. The mixture was stirred for 20 min at –70°, then a solution of 2,4,6-triisopropylbenzenesulphonyl azide (0.53 g) in THF (7 ml), previously cooled to –70° and acetic acid (0.14 ml) were added. The reaction mixture was allowed to stand at 23° and stirred for 15 h, ethyl acetate (70 ml) was then added and the solution was washed with water (2×50 ml) and brine (2×30 ml), dried and concentrated "in vacuo". The crude product was purified by flash chromatography (eluting with CH-EA 70:30) to give the title compound as a white foam (0.338 g). T.l.c. CH-EA (1:1), $R_f$=0.73.

Intermediate 41

1-(1-Adamantyl)methyl-3-amino-2,4-dioxo-5-phenyl-2,3,4,5-tetrahydro-1H-1,5-benzodiazepine A solution of the intermediate 40 (0.18 g) in ethanol (10 ml) and ethyl acetate (5 ml) was stirred under hydrogen, at 1 atm., in presence of 5% Pd/CaCO$_3$ (0.2 g), at 23°, for 3 h, then the catalyst was filtered off on a pad of celite and the organic layer was concentrated "in vacuo". The crude product was purified by flash chromatography (eluting with DCM-methanol 90:10) to give the title compound as a white foam (0.15 g). T.l.c. DCM-methanol (90:10), $R_f$=0.51.

Intermediate 42

1-(2,2-Dimethylethoxycarbonylmethyl)-2,4-dioxo-5-phenyl-2,3,4,5-tetrahydro-1H-1,5,-benzodiazepine Sodium hydride 80% dispersion in oil (0.155 g) was added portionwise to a solution of the compound (a) (1.022 g) in DMF (30 ml) previously cooled to 0°. The reaction was stirred for 15 min at 23°, then t-butyl bromoacetate (0.7 ml) was added. The solution was stirred at 23° for 1 h, then brine (100 ml) was added and the mixture extracted with ethyl acetate (3×30 ml), dried and concentrated "in vacuo". The crude product was purified by flash chromatography (eluting with CH-EA 60:40) to give the title compound as a white powder (1.31 g). T.l.c. CH-EA (60:40), $R_f$=0.4.

Intermediate 43

3-Azido-1-(2,2-dimethylethoxycarbonylmethyl)-2,4-dioxo-5-phenyl-2,3,4,5-tetrahydro-1H-1,5-benzodiazepine A solution of the intermediate 42 (0.5 g) in THF (6 ml), cooled to −70°, was added dropwise to a solution of potassium tert-butoxide (0.168 g) in THF (6 ml) cooled to −70°, under a nitrogen atmosphere. The reaction mixture was stirred for 30min at −70°, then a solution of 2,4,6-triisopropylbenzenesulphonyl azide (0.556 g) in THF (6 ml), previously cooled to −70° and acetic acid (0.078 ml) were added. The reaction mixture was allowed to stand at 23° and stirred for 18 h, ethyl acetate (30 ml) was added and the solution was washed with brine (3×100 ml), a saturated solution of sodium hydrogen carbonate (20 ml), brine (20 ml), dried and concentrated "in vacuo". The crude product was purified by flash chromatography (eluting with CH-EA 70:30) to give the title compound as a white foam (0.5 g). T.l.c. CH-EA (1:1), $R_f$=0.36.

Intermediate 44

3-Amino-1-(2,2-Dimethylethoxycarbonylmethyl)-2,4-dioxo-5-phenyl-2,3,4,5-tetrahydro-1H-1,5-benzodiazepine A solution of the intermediate 43 (0.354 g) in a mixture of ethanol (10 ml) and ethyl acetate (2 ml) was stirred under hydrogen, at 1 atm., in presence of 5% Pd/CaCO₃ (0.183 g), at 23°, for 3 h, then more 5% Pd/CaCO₃ (0.183 g) was added and the reaction stirred for 15 h. The catalyst was filtered off on a pad of celite, washing with dichloromethane (9 ml) and methanol (5 ml) and the organic layer was concentrated "in vacuo". The crude product was purified by flash chromatography (eluting with DCM-methanol 96:4) to give the title compound as a white foam (0.33 g). T.l.c. DCM-methanol (95:5), $R_f$=0.5.

Intermediate 45

1-(3,3-dimethylbutyl)-2,4-dioxo-5-phenyl-2,3,4,5-tetrahydro-1H-1,5-benzodiazepine Sodium hydride 80% dispersion in oil (0.100 g) was added portionwise to a solution of the compound (a) (0.7 g) in DMF (60 ml). The reaction mixture was stirred for 30 min, then a solution of 3,3-dimethylbutyl methanesulfonate (0.575 g) in DMF (3 ml) was added. The reaction mixture was stirred at 90° for 50 min, at 23° for 15 h, at 90° for 2 h and at 140° for 45 min, then concentrated. The residue was diluted with water (30 ml) and brine (20 ml) and extracted with ethyl acetate (150 ml); the organic layer was washed with water (2×50 ml) and brine (50 ml), dried and concentrated "in vacuo". The crude product was purified by flash chromatography (eluting with CH-EA 1:1) to give the title compound as a white foam (0.4 g). Tlc. CH-EA (1:1), $R_f$=0.39.

Intermediate 46

3-Azido-1-(3,3-dimethylbutyl)-2,4-dioxo-5-phenyl-2,3,4,5-tetrahydro-1H-1,5-benzodiazepine A solution of potassium tert-butoxide (0.146 g) in THF (7 ml), cooled to −70°, was added dropwise to a solution of the intermediate 45 (0.4 g) in THF (15 ml), cooled to −70°, under a nitrogen atmosphere. The solution was stirred for 20 min at −70°, then a solution of 2,4,6-triisopropylbenzenesulphonyl azide (0.530 g) in THF (7 ml), previously cooled to −70° and acetic acid (0.139 ml) were added. The reaction mixture was allowed to stand at 23° and stirred for 18 h, then ethyl acetate (75 ml) was added and the solution was washed with water (2×50 ml) and brine (2×30 ml), dried and concentrated "in vacuo". The crude product was purified by flash chromatography (eluting with CH-EA 30:70) to give the title compound as a white foam (0.338 g). T.l.c. CH-EA (1:1), $R_f$=0.73.

Intermediate 47

3-Amino-1-(3,3-dimethylbutyl)-2,4-dioxo-5-phenyl-2,3,4,5-tetrahydro-1H-1,5-benzodiazepine A solution of the intermediate 46 (0.298 g) in a mixture of ethanol (18 ml) and ethyl acetate (7 ml) was stirred under hydrogen, at 1 atm., in presence of 5% Pd/CaCO₃ (0.186 g), at 23°, for 1.5 h, then more 5% Pd/CaCO₃ (0.180 g) was added and the reaction stirred for 1 h. The catalyst was filtered off on a pad of celite, washing with ethanol (20 ml) and the organic layer was concentrated "in vacuo". The crude product was purified by flash chromatography (eluting with DCM-methanol 90:10) to give the title compound as a white foam (0.205 g).T.l.c. DCM-methanol (90:10), $R_f$=0.46.

Intermediate 48

1-(3,3-Dimethylbutyl)-2,4-dioxo-3-isocyanato-5-phenyl-2,3,4,5-tetrahydro-1H-1,5-benzodiazepine To a solution of the intermediate 47 (0.3 g) in dichloromethane (20 ml), a 1.93M solution of COCl₂ in toluene (10 ml) was added. The reaction mixture was stirred for 5 h at 23°, then concentrated "in vacuo" at 50° for 3 h to obtain the title compound as a white foam (0.370 g). IR: 2218 (N=C=O); 1693, 1668 (C=O), (C=C) cm⁻¹;

Intermediate 49

1-(3,3-Dimethylbutyl)-2,4-dioxo-5-phenyl-3-phenyloxycarbonylamino-2,3,4,5-tetrahydro-1H-1,5-benzodiazepine To a solution of the intermediate 47 (1 g) in dichloromethane (50 ml), pyridine (0.46 ml) and phenylchloroformate (0.7 ml) were added. The reaction mixture was stirred for 30 min at 23°, then washed with a 1% solution of hydrochloric acid (20 ml), a 5% solution of sodium hydrogen carbonate (20 ml), water (20 ml), brine (20 ml), dried and concentrated "in vacuo". The crude product was tritured with acetonitrile (10 ml) to obtain the title compound as a white powder (1.2 g). T.l.c. CH-EA (1:1) $R_f$=0.8.

Intermediate 50

1-[2-(1-adamantyl)ethyl]-2,4-dioxo-5-phenyl-3-phenyloxycarbonylamino-2,3,4,5-tetrahydro-1H-1,5-benzodiazepine To a solution of the intermediate 53 (0.1 g) in dichloromethane (10 ml), pyridine (0.03 ml) and phenylchloroformate (0.01 ml) were added. The reaction mixture was stirred for 2 h at 23°, then diluted with dichloromethane (30 ml), washed with a saturated solution of ammonium chloride (30 ml) and brine (40 ml), dried and concentrated "in vacuo". The crude product was triturated with acetonitrile (10 ml) to obtain the title compound as a white powder (0.05 g). T.l.c. CH-EA (1:1) $R_f$=0.77.

Intermediate 51

1-[2-(1-Adamantyl)ethyl]-2,4-dioxo-5-phenyl2,3,4,5-tetrahydro-1H-1,5-benzodiazepine Sodium hydride 80% dispersion in oil (0.15 g) was added portionwise to a solution of the compound (a) (0.8 g) in DMF (20 ml) previously cooled to 0°. The reaction was stirred for 15 min at 0°, a solution of 2-(1-adamantyl)ethyl bromide (0.8 g) in DMF (10 ml) was added dropwise, the mixture was stirred at 23° for 8 h, then diluted with DMF (20 ml) heated at 80° for 1 h and allowed to stand at 23° for 2 days. ethyl acetate (200 ml) was added and the solution was washed with brine (3×100 ml), dried and concentrated "in vacuo". The crude product was purified by flash chromatography (eluting with CH-EA 70:30) to give the title compound as a white foam (0.45 g). T.l.c. CH-EA (1:1), $R_f$=0.42.

Intermediate 52

1-[2-(1-Adamantyl)ethyl]-3-azido-2,4-dioxo-5-phenyl-2,3,4,5-tetrahydro-1H-1,5-benzodiazepine A solution of potassium tert-butoxide (0.2 g) in THF (10 ml) was added dropwise to a solution of the intermediate 51 (0.67 g) in THF (20 ml), cooled to −70°, under a nitrogen atmosphere. The mixture was stirred for 20 min at −70°, then a solution of 2,4,6-triisopropylbenzenesulphonyl azide (0.65 g) in THF (10 ml), previously cooled to −70° and acetic acid (0.18 ml) were added. The reaction mixture was allowed to stand at 23° and stirred for 15 h, then EA (150 ml) was added and the solution was washed with a 5% solution of sodium hydrogen carbonate (80 ml) and brine (100 ml), dried and concentrated "in vacuo". The crude product was purified by flash chromatography (eluting with CH-EA 90:10) to give the title compound as a white foam (0.71 g). T.l.c. CH-EA (1:1), $R_f$=0.86.

Intermediate 53

1-[2-(1-Adamantyl)ethyl]-3-amino-2,4-dioxo-5-phenyl-2,3,4,5-tetrahydro-1H-1,5-benzodiazepine A solution of the intermediate 52 (0.71 g) in ethanol (30 ml) and ethyl acetate (15 ml) was stirred under hydrogen, at 1 atm., in presence of 5% Pd/CaCO$_3$ (0.7 g), at 23°, for 3 h.

The catalyst was filtered off on a pad of celite, washing with methanol (50 ml) and the organic layer was concentrated "in vacuo". The crude product was purified by flash chromatography (eluting with DCM-methanol 90:10) to give the title compound as a white foam (0.5 g). T.l.c. DCM-methanol (90:10), $R_f$=0.62.

Intermediate 54

1-(2,3-Dimethyl)butyl-2,4-dioxo-5-phenyl-2,3,4,5-tetrahydro-1H-1,5-benzodiazepine Sodium hydride 80% dispersion in oil (0.06 g) was added portionwise to a solution of the compound (a) (0.38 g) in DMF (10 ml). The reaction was stirred at 23° for 1 h, then 2,3-dimethylbutyl methanesulfonate (0.32 g) was added. The mixture was stirred at 23° for 15 h, then water (70 ml) was added and the solution was extracted with ethyl acetate (2×50 ml) and the combined organic layer were washed with brine (2×50 ml), dried and concentrated "in vacuo". The crude product was purified by flash chromatography (eluting with CH-EA 80:20) to give the title compound as a white foam (0.23 g). T.l.c. CH-EA (1:1), $R_f$=0.4.

Intermediate 55

3-Azido-1-(2,3-dimethylbutyl)-2,4dioxo-5-phenyl-2,3,4,5-tetrahydro-1H-1,5-benzodiazepine A solution of potassium tert-butoxide (0.121 g) in THF (10 ml) was added to a solution of the intermediate 54 (0.33 g) in THF (20 ml), cooled to −70°, under a nitrogen atmosphere. The mixture was stirred for 30 min at −70°, then a solution of 2,4,6triisopropylbenzenesulphonyl azide (0.349 g) in THF (10 ml), previously cooled to −70° and, after 20 min, acetic acid (0.06 ml) were added. The reaction mixture was allowed to stand at 23° and stirred for 24 h; ethyl acetate (50 ml) was added and the solution washed with a 5% solution of sodium hydrogen carbonate (2×50 ml) and brine (2×50 ml), dried and concentrated "in vacuo". The crude product was purified by flash chromatography (eluting with CH-EA 80:20) to give the title compound as a white foam (0.1 g). T.l.c. CH-EA (1:1), $R_f$=0.53.

Intermediate 56

3-Amino-1-(2,3-dimethylbutyl)-2,4-dioxo-5-phenyl-2,3,4,5-tetrahydro-1H-1,5-benzodiazepine A solution of the intermediate 55 (0.19 g) in ethanol (15 ml) and ethyl acetate (3 ml) was stirred under hydrogen, at 1 atm., in presence of 5% Pd/CaCO$_3$ (0.18 g), at 23°, for 4 h. The catalyst was filtered off on a pad of celite, washed with ethyl acetate and the organic layer was concentrated "in vacuo". The erode product was purified by flash chromatography (eluting with EA-methanol 90:10) to give the title compound as a white foam (0.95 g). T.l.c. EA-methanol (90:10), $R_f$=0.55.

Intermediate 57

1-Butyl-2,4-dioxo-5-phenyl-2,3,4,5-tetrahydro-1H-1,5-benzodiazepine

Sodium hydride 80% dispersion in oil (0.03 g) was added portionwise to a solution of the compound (a) (0.3 g) in DMF (18 ml) at 0°, under a nitrogen atmosphere. The reaction was allowed to stand at 23° for 30 min, then a solution of 1-bromobutane (0.154 ml) in DMF (3 ml) was added dropwise. The mixture was stirred at 23° for 2 h, then water (30 ml) was added and the solution was extracted with ethyl acetate (2×60 ml) and the combined organic layer were dried and concentrated "in vacuo". The crude product was purified by flash chromatography (eluting with CH-EA 60:40) to give the title compound as a white foam (0.057 g). T.l.c. CH-EA (70:30), $R_f$=0.53.

Intermediate 58

3-Azido-1-butyl-2,4-dioxo-5-phenyl-2,3,4,5-tetrahydro-1H-1,5-benzodiazepine

A solution of potassium tert-butoxide (0.0418 g) in THF (2 ml) was added to a solution of the intermediate 57 (0.104 g) in THF (2 ml), cooled to −70°, under a nitrogen atmosphere. The mixture was stirred for 30 min at −70°, then a solution of 2,4,6-triisopropylbenzenesulphonyl azide (0.136 g) in THF (10 ml), previously cooled to −70° and acetic acid (0.019 ml) were added. The reaction mixture was allowed to stand at 23° and stirred for 24 hrs, ethyl acetate (50 ml) added and the solution washed with a 5% solution of sodium hydrogen carbonate (10 ml), brine (10 ml), dried and concentrated "in vacuo". The crude product was purified by flash chromatography (eluting with CH-EA 80:20) to give the title compound as a white foam (0.043 g). T.l.c. CH-EA (60:40), $R_f$=0.67.

Intermediate 59

3-amino-1-butyl-2,4-dioxo-5-phenyl-2,3,4,5-tetrahydro-1H-1,5-benzodiazepine

A solution of the intermediate 58 (0.217 g) in ethanol (4 ml) and ethyl acetate (10 ml) was stirred under hydrogen, at 1 atm., in presence of 5% Pd/CaCO$_3$ (0.18 g), at 23°, for 10 h. The catalyst was filtered off on a pad of celite, washed with ethyl acetate (3×5 ml) and ethanol (3×5 ml) and the organic layer was concentrated "in vacuo". The crude product was purified by flash chromatography (eluting with EA-methanol 90:10) to give the title compound as a white foam (0.094 g). Tlc. EA-methanol (95:5), $R_f$=0.25.

Intermediate 60

2,4-Dioxo-5-phenyl-1-(3-methyl-2-oxo)butyl-2,3,4,5-tetrahydro-1H-1,5-benzodiazepine Sodium hydride 80% dispersion in oil (0.4 g) was added portionwise to a solution of the compound (a) (2 g) in DMF (50 ml), previously cooled to 0 C. The reaction was stirred for 15 min at 0°, then a solution of 1-bromo-3-methyl-2-oxobutane (2.6 g) in DMF (10 ml) was added dropwise, the mixture was stirred at 0 C. for 45 min, ethyl acetate (450 ml) added and the solution washed with brine (4×100 ml), dried and concentrated "in vacuo". The crude product was purified by flash chromatography (eluting with CH-EA 1:1) to give the title compound as a white foam (2.3 g). T.l.c. CH-EA (1:1), $R_f$=0.19.

Intermediate 61

3-Azido-2,4-dioxo-1-(3-methyl-2-oxo)butyl-5-phenyl-2,3,4,5-tetrahydro-1H-1,5-benzodiazepine A solution of potassium tert-butoxide (0.185 g) in THF (10 ml) was added dropwise to a solution of the intermediate 60 (0.5 g) in THF (20 ml), cooled to −70°, under a nitrogen atmosphere. The mixture was stirred for 20 min at −70°, then a solution of 2,4,6-triisopropylbenzenesulphonyl azide (0.688 g) in THF (10 ml), previously cooled to −70° and acetic acid (0.2 ml) were added. The reaction mixture was allowed to stand at 23° and stirred for 15 h, ethyl acetate (400 ml) added and the solution was washed with brine (3×100 ml), dried and concentrated "in vacuo". The crude product was purified by flash chromatography (eluting with CH-EA 1:1) to give the title compound as a foam. T.l.c. CH-EA (1:1), $R_f$=0.51.

Intermediate 62

3-Amino-2,4-dioxo-1-(3-methyl-2-oxo)butyl-5-phenyl-2,3,4,5-tetrahydro-1H-1,5-benzodiazepine A solution of the intermediate 61 (0.85 g) in ethanol (35 ml) was stirred under hydrogen, at 1 atm., in presence of 5% Pd/CaCO$_3$ (1 g), at 23°, for 2 h. The catalyst was filtered off on a pad of celite, washing with ethanol (30 ml) and the organic layer was concentrated "in vacuo". The crude product was purified by flash chromatography (eluting with DCM-methanol 90:10) to give the title compound as a white foam (0.5 g). T.l.c. DCM-ethanol (95:5), $R_f$=0.56.

Intermediate 63

N-[2,4-Dioxo-1-(3-methyl-2-oxo)butyl-5-phenyl-2,3,4,5-tetrahydro-1H-1,5-benzodiazepin-3-yl]-N'-phenylurea Phenyl isocyanate (0.2 ml) was added to a solution of the intermediate 62 (0.43 g) in dry acetonitrile (15 ml) under a nitrogen atmosphere. The mixture was stirred at 23° for 1 h and the formed precipitate filtered washing with acetonitrile (30 ml) to give the title compound as a white solid (0.37 g). T.l.c. CH-EA (1:1), $R_f$=0.27.

Intermediate 64

2,4-Dioxo-1-(3-methylbut-1-yl)-5-phenyl-2,3,4,5-tetrahydro-1H-1,5-benzodiazepine NaH 80% dispersion in oil (0.057 g) was added to a solution of 2,4-dioxo-5-phenyl-2,3,4,5-tetrahydro-1H-1,5-benzodiazepine (0.40 g) in dry DMF (15 ml). The reaction mixture was cooled at 0° and stirred for 15 min, 1-bromo-3-methyl-butane (0.23 ml) in dry DMF (4 ml) was added and stirring continued for 2 h. The reaction mixture was then diluted with water (100 ml), extracted with ethyl acetate (3×100 ml), washed with brine (2×50 ml), dried and concentrated in vacuo to give an oil (0.75 g) which was purified by flash chromatography (eluting with CH-EA 60:40) to give the title compound as a white solid (0.44 g). T.l.c. CH-EA (1:1), Rf. 0.36

Intermediate 65

3-Azido-2,4-Dioxo-1-(3-methylbut-1-yl)-5-phenyl-2,3,4,5-tetrahydro-1H-1,5-benzodiazepine A solution of the intermediate 64 (0.397 g) in dry THF (7 ml) was added to potassium tert-butoxide (0.154 g) in dry THF (6 ml) cooled at −78°. The reaction mixture was stirred for 30 min, then a cooled (−78°) solution of 2,4,6-triisopropyl-benzenesulphonylazide (0.49 g) in dry THF (7 ml) was added. After 5 min glacial acetic acid (0.07 ml) was added and the solution was allowed to warm at 23° and stirred for 24 h. The reaction mixture was diluted with ethyl acetate (40 ml) and washed with water (20 ml) saturated sodium hydrogen carbonate solution (20 ml) and brine (20 ml). The combined organic extracts were dried and concentrated in vacuo to give an oil (0.7 g). Purification by flash chromatography (eluting with CH-EA 60:40) gave the title compound as a white solid (0.25 g) T.l.c. CH-EA (60;40), Rf 0.3.

Intermediate 66

3-Amino-2,4-Dioxo-1-(3-methylbut-1-yl)-5-phenyl-2,3,4,5-tetrahydro-1H-1,5-benzodiazepine 5% Pd/CaCO3 (0.61 g) was added to a solution of intermediate 65 (1.21 g) in ethyl acetate (60 ml) and ethanol (60 ml) and the reaction mixture was hydrogenated at 1 atm for 3 h and 30 min. The catalyst was filtered off and the solvent evaporated in vacuo to give the title compound as a pale yellow foam (1.14 g). T.l.c. DCM-methanol (95:5), Rf 0.55.

Intermediate 67

3-Amino-2,4-Dioxo-1-(3-methylbut-1-yl)-5-phenyl--2,3,4,5-tetrahydro-1H-1,5-benzodiazepine (1S)-(+)-10-camphorsulphonic salt To intermediate 66 (2.05 g) dissolved in hot ethyl acetate (35 ml), (1S)-(+)-10-camphorsulphonic acid was added. The resulting salt (5b) was crystallized out from the cool solution by dropwise addition of cyclohexane; the precipitate was filtered off and washed with cold cyclohexane to give a (+)/(−) 3/97 mixture of diastereomeric salt (1.11 g) and mother liquors. Recrystallization (twice) from 2-propanol afforded the pure title compound (0.49 g) IR: 2750–2600 (NH3); 1736, 1713, 1700 (C=O) cm−1; $^1$H-NMR,: 9.0–7.4 (m); 7.5 (d): 7.45–7.2 (m); 7.18 (t); 6;97 (d); 5.05 (s); 4.58 (m); 3.68 (m); 3.20 (m); 2.72 (m); 2.42 (m); 2.22 (m); 2.0 (m); 1.2 (m); 1.0–0.7 (m).

Intermediate 68

(−)3-Amino-2,4-Dioxo-1-(3-methylbut-1-yl)-5-phenyl--2,3,4,5-tetrahydro-1H-1,5-benzodiazepine Intermediate 67 (0.47 g) was suspended in ethyl acetate and washed with 5% ammonia solution (2×20 ml) and brine (2×20 ml). The organic layer was dried and concentrated in vacuo to give the title compound as a white foam (0.27 g). T.l.c. DCM-methanol (9 5:5), Rf 0.55. [alpha]$_D$=−114. IR: 3377 (NH2), 1705–1670 (C=C), 1593 cm−1; 1H-NMR: 7.5–7.1(m); 6.95 (dd); 4.55(m), 4.23 (s); 3.7 (m); 1.8(m); 1.64–1.4(m); 0.92(d); 0.89 (d)

Intermediate 69

3-Amino-2,4-Dioxo-1-(3-methylbut-1-yl)-5-phenyl--2,3,4,5-tetrahydro-1H-1,5-benzodiazepine (1R)-(−)-10-camphorsulphonic salt The mother liquors obtained after the initial precipitation of intermediate 67 were evaporated to dryness to give a solid (2.19 g). The residue was taken up in ethyl acetate (30 ml), extracted with a 5% ammonia solution (20 ml) and washed with brine (20 ml), the organic layer dried and evaporated in vacuo to give a residue (1.0 g). (1R)-(−)-10-camphorsulphonic acid in ethyl acetate (6 ml) was added to the solution of the residue (1 g) in ethyl acetate (5 ml ) and the resulting solution was stirred at 0° for 2 h. The obtained precipitate was filtered off, washed with ethyl acetate (20 ml) and dried to give the title compound (0.97 g). 1H-NMR: 9.0–7.2(m); 7.5 (d): 7.45–7.2 (m); 7.18 (t); 6.97 (d); 5.04 (s); 4.6 (m); 3.68 (m); 3.20 (m); 2.70 (m); 2.42 (m); 2.22 (m); 2.0–1.8(m); 1.7–1.2 (m); 1.0–0.7(m).

Intermediate 70

(+)-3-Amino-2,4-Dioxo-1-(3-methylbut-1-yl)-5-phenyl--2,3,4,5-tetrahydro-1H-1,5-benzodiazepine Intermediate 69 (0.95g ) was suspended in ethyl acetate (130 ml), washed with a 5% ammonia solution (70 ml) and stirred at 23° for 10 min. The organic layer was separated, washed with brine (3×70 ml) dried and concentrated in vacuo to give the crude compound. Purification by flash chromatography (eluting with acetone-methanol 9:1) gave the title compound as a white foam (0.51). [alpha]$_D$; IR: 3375 (NH$_2$), 1715–1661(C=C), 1591 cm−1; 1H-NMR: 7.5–7.1(m); 6.95 (dd); 4.6–4.5(m), 4.24 (s); 3.8–3.65(m); 1.8(m); 1.62–1.4(m); 0.92(d); 0.89 (d).

Intermediate 71

3-Amino-2,4-dioxo-5-(2-fluorophenyl)-1-(3-methylbut-1-yl)-2,3,4,5-tetrahydro-1H-1,5-benzodiazepine, (1R)-(−)-10-camphorsulfonate A hot solution of (1R)-(−); 10-camphorsulfonic acid (1.685 g) in ethyl acetate (15 ml) was added, dropwise over 30', to a solution of the intermediate 3 (3.0 g) in ethyl acetate (7 ml) previously heated to 90 to under a nitrogen atmosphere. The resulting solution was heated to 90 for 10', then concentrated in vacuo. The residue triturated with EE-petroleum gave a (+)/(−) 50/50 mixture of diastereomeric salt (4.65 g). Recrystallization from 2-propanol gave the title compound (0.9 g). M.p.216–7. [alpha]D=+67.8.

Intermediate 72

3-(+)-Amino-2,4-dioxo-5-(2-fluorophenyl)-1-(3-methylbut-1-yl)-3,4,5-tetrahydro-1H-1,5-benzodiazepine Intermediate 70 (0.85 g) was dissolved in a 5% ammonia solution (50 ml) and extracted with ethyl acetate (2×40 ml). The combined organic extracts were washed with brine (60 ml), dried and concentrated in vacuo to give the title compound as a white foam (0.5 g). M.p. 125°–6°.

T.l.c. DCM-methanol (30:1), Rf 0.38. [alpha]D=+115.2.

Intermediate 73

2-(Adamant-2-yl)amino-diphenylamine

Sodium borohydride (1.873 g) was added portionwise to a mixture of 2-aminodiphenylamine 1 (0.61 g), sodium acetate trihydrate (1.368) and 2-adamantanone (0.5 g) in acetic acid (2.1 ml), water (8 ml) and ethanol (6.5 ml) cooled to 0. The reaction mixture was Stirred at 23 for 1 h, then diluted with ethyl acetate (100 ml). The organic layer was washed with water (30 ml), a 10% solution of sodium hydroxide (2×25 ml), water (30 ml) and brine (20 ml), dried and concentrated in vacuo to yield a residue which was taken up in DCM and the unreacted solid 2-adamantanone was removed by filtration. The filtrate was concentrated in vacuo and purified by flash chromatography (eluting with CH-EA 95:5) to give the title compound as a yellow solid (0.185 g).

T.l.c. CH-EA (90:10), Rf 0.73.

Intermediate 74

1-(Adamant-2-yl)-2,4-dioxo-5-phenyl-3-phenyl-hydrazono-2,3,4,5-tetrahydro-1H-1,5-benzodiazepine The intermediate 73 (0.96 g) and 2-phenylhydrazonomalonyldichloride (0.89 g) were each taken up in THF (10 ml) and dropped in a flask containing THF (50 ml) maintained at 0 under a nitrogen atmosphere. After complete addition the solution was allowed to warm to room temperature and then heated to 50 for 3 h. The reaction mixture was concentrated in vacuo to give an oil, which was purified by flash chromatography (eluting with CH-EA 90:10) to give the title compound as a yellow solid (0.758 g). T.l.c CH-EA (80:20), Rf 0.60.

Intermediate 75

1-(Adamant-2-yl)-3-amino-2,4-dioxo-5-phenyl-2,3,4,5-tetrahydro-1H-1,5-benzodiazepine A suspension of the intermediate 74 (0.745 g) in glacial acetic acid (10 ml) was added to a mixture of zinc dust (0.956) in glacial acetic acid (5 ml), cooled to 0. The mixture was stirred at 23 for 3 h, then diluted with water (100 ml) and decanted from zinc. Solid sodium carbonate was added until pH=9 and the mixture extracted with ethyl acetate (3×100 ml). The combined organic extracts were dried and concentrated in vacuo. The residue was triturated with ethyl acetate to give the title compound as a white solid (0.51 g). M.p. 231°–3° (dec). T.l.c. DCM-methanol (90:10), Rf 0.61.

Intermediate 76

1-(Adamant-2-yl)-2,4-dioxo-3-isocyanate-5-phenyl-2,3,4,5-tetrahydro-1H-1,5-benzodiazepine Phosgene in toluene (1.93M solution, 10 ml) was added to a solution of the intermediate 75 (0.285 g) in dichloromethane (10 ml); the resulting solution was stirred at 23 for 4 h, then concentrated in vacuo at 50 for 2.5 h to give the title compound as a white foam (0.29 g).

IR: 2220 (N=C), 1697 and 1676 (C=O) cm$^{-1}$; $^1$H-NMR: 7.50–7.15 (m); 7.05–6.95(m); 4.7 (s); 4.55 (m); 3.05 (m); 2.35 (m); 1.95–1.1 (m).

Intermediate 77

2-(2-cyclopentyl-ethyl)-amino-2'fluoro-diphenylamine

Sodium borohydride (17.86 g) was added portionwise to a mixture of 2-amino-2'-fluoro-diphenylamine (6.47 g), sodium acetate trihydrate (4.24 g) and cyclopentylacetaldehyde (3.58 g) in acetic acid (19.6 ml), water (76 ml) and ethanol (60 ml) cooled to 0°. The reaction mixture was stirred at 23° for 1 h and 30 min., then diluted with ethyl acetate (200 ml). The organic layer was washed with water (70 ml), a 10% solution of sodium hydroxide (70 ml), and brine (50 ml), dried and concentrated in vacuo to yield a residue which was purified by flash chromatography (eluting with CH-EA 9:1) to give the title compound as a yellow oil (3.35 g). T.l.c. CH-EA (9:1), RF 0.78

Intermediate 78

1-(2-Cyclopentyl-ethyl)-2,4-dioxo-5-(2-fluorophenyl)-3-phenylhydrazono-2,3,4,5-tetrahydro-1H-1,5-benzodiazepine The intermediate 77 (3.30 g) and 2-phenylhydrazonomalonyldichloride (3.25 g) were each taken up in THF (25 ml) and dropped in a flask containing THF (150 ml) maintained at 0° under a nitrogen atmosphere. After complete addition the solution was allowed to warm to 23° C.; the reaction mixture was then heated to 55° for 3 h and concentrated in vacuo. The residue was taken up in cyclohexane/EA 7/3 (40 ml); the precipitate was filtered off and washed with cyclohexane to give the title compound as a yellow solid (3.75 g). T.l.c. CH-EA (1:1), Rf 0.71.

Intermediate 79

3-Amino-1-(2-cyclopentyl-ethyl)-2,4-dioxo-5-(2-fluoro)phenyl-2,3,4,5-tetrahydro-1H-1,5-benzodiazepine To a suspension of Zinc dust (4.70 g) cooled to 0°, intermediate 78 (3.70 g) in glacial acetic acid (50 ml) was added. The mixture was stirred at 23° for 5 h, then, diluted with water (250 ml) and decanted from the zinc. Solid sodium carbonate was added until Ph 9, then EA (300 ml) was added and the organic extracts were,dried and concentrated in vacuo to give a residue which was purified by flash chromatography (eluting with CH-EA 1:1) then with DCM/methanol 9:1 to give the title compound (2.55 g) as a white foam. T.l.c. DCM-methanol (90: 10), Rf 0.63.

Intermediate 80

1-(2-cyclopentyl-ethyl)-2,4-dioxo-5-(2-flurophenyl)-3-isocyanate-2,3,4,5-tetrahydro-1H-1,5-benzodiazepine Phosgene in toluene (1.93M solution, 25 ml) was added to a solution of the intermediate 79 (0.734 g) in dry dichloromethane (60 ml); the resulting solution was stirred at 23° for 5 h, then concentrated in vacuo at 50° for 3 h to give the title compound as a white solid. T.l.c. DCM-methanol (90:10), Rf 0.63.

Intermediate 81

2-(Bicyclo[2.2.1]-5-heptene-2-yl-methyl)-amino-diphenylamine

To a solution of 2-aminodiphenylamine (3.06 g) in toluene (100 ml) 5-norbornene-2-carboxaldehyde (2 ml) was added and the mixture was refluxed under a nitrogen atmosphere, in the presence of 4A molecular sieves, for 6 hrs. The solution was decanted from the sieves and the solvent was evaporated. The residue was dissolved in methanol (loom) and sodium borohydride (5.70 g) was added portionwise. The mixture was stirred at 23° for 12 hr., diluted with ethyl acetate (100 ml), washed with a 10% potassium carbonate solution (2×100 ml) and brine (100 ml), then dried and concentrated in vacuo. The crude material was purified by flash chromatography (eluting with CH-EA 95:5) to give the title compound (0.92 g) as a yellow glass. T.l.c. CH-EA (95:5), R$_f$ 0.56.

Intermediate 82

1-(Bicyclo[2.2.1]-5-heptene-2-ylmethyl)-2,4-dioxo-5-phenyl-3-phenylhydrazono-2,3,4,5-tetrahydro-1H-1,5-benzodiazepine Intermediate 81 (0.85 g) and 2-phenylhydrazonomalonyidichloride (0.87 g) were each taken up in dry THF (40 ml) and dropped into a flask containing THF (10 ml). The mixture was refluxed, under nitrogen, for 2 hrs, then it was diluted with ethyl acetate (50 ml) and washed with a 5% sodium bicarbonate solution (50 ml) and brine (50 ml). The organic layer was dried, concentrated in vacuo and purified by flash chromatography (eluting with CH-EA 9:1) to give the title compound (1.27 g) as a yellow foam. M.p. 149°–151°. T.l.c. (CH-EA 8:2) Rf 0.34.

Intermediate 83

3-Amino-1-(Bicyclo[2.2.1]-5-heptene-2-yl-methyl)-2,4-dioxo-5-phenyl-2,3,4,5-tetrahydro-1H-1,5-benzodiazepine Zinc dust (1.5 g) was added to a solution of the intermediate 82 (0.49 g) in glacial acetic acid (20 ml). The mixture was stirred at 23° for 12 hrs, then it was filtered through a pad of celite. The filtrate was concentrated in vacuo; the residue was taken up in ethyl acetate (70 ml) and washed with a 10% sodium hydroxide solution (2×50 ml) and brine (2×50 ml), then dried and concentrated in vacuo. Purification by flash chromatography (eluting with EA-MeOH 9:1) afforded the title compound (0.26 g) as a light yellow foam. T.l.c. (EA-MeOH 9:1), $R_f$ 0.37.

Intermediate 84

3-Amino-1-(bicyclo[2.2.1]-2-heptylmethyl)-2,4-dioxo-5-phenyl-2,3,4,5-tetrahydro-1H-1,5-benzodiazepine The intermediate 82 (0.506 g), suspended in methanol (20 ml), was hydrogenated at 1 atmosphere, in the presence of 5% Pd/C (0.271 g) and concentrated hydrochloric acid (1.6 ml), for 7 h. Then, the mixture was filtered through a pad of celite and the solvents were evaporated. The residue was taken up in ethyl acetate (100 ml) and washed with a 5% sodium hydroxide solution (2×100 ml) and brine (100 ml); the organic layer was dried, concentrated in vacuo and purified by flash chromatography (eluting with EA-MeOH 9:1) to give the title compound (0.31 g) as a white foam.

T.l.c. (EA-MeOH 9:1) $R_f$ 0.55.

Intermediate 85

2-[Bicyclo[2.2.1]-2-heptyl]amino-diphenylamine

A mixture of 2-aminodiphenylamine (5.0 g), 2-norbornanone (3.0 g) and molecular sieves in dry toluene (200 ml) was heated to 1200 for 6 h. The mixture was allowed to cool to room temperature, filtered and the solution concentrated in vacuo. The residue was dissolved in ethanol (200 ml), then sodium borohydride (3.0 g) was added portionwise. The resulting mixture was stirred at 23° for 30 min, diluted with water (150 ml) and extracted with ethyl acetate (300 ml). The organic layer was washed with brine (2×200 ml), dried and concentrated in vacuo to an oil which was purified by flash chromatography (eluting with CH-EA 9:1) to give the title compound as a yellow oil (3.5 g). T.l.c. CH-EA (9:1), Rf 0.74.

Intermediate 86

1-[Bicyclo[2.2.1]-2-heptyl]-2,4-dioxo-5-phenyl-3-phenylhydrazono-2,3,4,5-tetrahydro-1H-1,5-benzodiazepine The intermediate 85 (3.77 g) and the 2-phenylhydrazonomalonyldichloride (3.98 g) were each taken up in THF (70 ml) and dropped into a flask containing THF (60 ml) under a nitrogen atmosphere. After complete addition the solution was heated to 50° for 1 h. The solution was concentrated in vacuo to an oil which was purified by flash chromatography, (eluting with CH-EA 8:2) to give the title compound as a yellow solid (6.0 g). M.p.110°–111° T.l.c. CH-EA (7:3), Rf 0.72 and 0.66.

Intermediate 87

3-Amino-1-[bicyclo[2.2.1]-2-heptyl]-2,4-dioxo-5-phenyl2,3,4,5-tetrahydro-1,5-benzodiazepine Zinc dust (3.26 g) was added to a solution of the intermediate 86 (3.0 g) in glacial acetic acid (30 ml). The mixture was stirred at 23° for 4 h, then decanted from zinc. The solution was basified until pH=9 using 10% sodium hydroxide solution and extracted with ethyl acetate (2×100 ml). The combined organic extracts were washed with brine (150 ml), dried and concentrated in vacuo to a residue which was triturated with diethyl ether to give the title compound as a white solid (1.34 g). M.p. 172°–3°. T.l.c. EA-MeOH (95:5), Rf 0.3.

Intermediate 88

2-(2-Adamantylmethyl)amino-diphenylamine

A solution of sodium acetate trihydrate (6.45 g) and acetic acid (5 ml) in water was added to a mixture of 2-adamantanecarboxaldehyde (2.6 g) and 2-aminodiphenylamine 1 (2.84 g) in ethanol (130 ml). Then sodium borohydride (5.97 g) was added portionwise. The resulting mixture was stirred at 23° for 6 h, then diluted with water (80 ml) and extracted with ethyl acetate (2×150 ml). The combined organic extracts were washed with brine (150 ml), dried and concentrated in vacuo to a residue, which was purified by flash chromatography to give the title compound as a yellow oil (2.15 g). T.l.c. CH-EA (8:2), Rf 0.86.

Intermediate 89

1-(2-Adamantylmethyl)-2,4-dioxo-5-phenyl-3-phenylhydrazono-2,3,4,5-tetrahydro-1H-1,5-benzodiazepine A solution of 2-phenylhydrazonomalonyldichloride (1.78 g) in THF (50 ml) was added to a solution of the intermediate 88 (2.0 g) in THF (50 ml) under a nitrogen atmosphere. The resulting solution was heated to 50° for 1 h., then concentrated in vacuo to a residue which was purified by flash chromatography (eluting with CH-EA 9:1) to give the title compound as a yellow solid (1.95 g). M.p.135°–6° (dec) T.l.c. CH-EA (8:2), Rf 0.48.

Intermediate 90

1-(2-Adamantylmethyl)-3-amino-2,4-dioxo-5-phenyl-2,3,4,5-tetrahydro-1H-1,5-benzodiazepine Zinc dust (1.84 g) was added to a solution of the intermediate 89 (1.9 g) in glacial acetic acid (20 ml). The mixture was stirred at 23C for 2 h, then decanted from zinc. The solution was basified until pH=9 using 10% sodium hydroxide solution and extracted with ethyl acetate (2×80 ml). The combined organic extracts were washed with brine (100 ml), dried and concentrated in vacuo to a residue which was purified by flash chromatography (eluting in gradient from CH-EA 1:1 to EA) to give the title compound as a yellow solid (0.95 g). M.p. 209°–210°. T.l.c. EA-MeOH (20:1), Rf 0.38.

Intermediate 91

5-Fluoro-N-(4-Fluorophenyl)2-nitro aniline.

A mixture of 2,4-difluoronitrobenzene (5.5 ml),4-fluoro aniline (14.2 ml) and sodium carbonate (5.3 g) was heated at 180° for 3 h. The reaction mixture was cooled to room temperature, then diluted with DCM, washed with water (50 ml), brine (2×50 ml) dried and evaporated under vacuum to give the crude compound (22.6 g), which was purified by flash chromatography with CH-EA 4/1 to give the title compound as an orange solid (12.35 g).M.p. 115°–6° T.l.c. CH-EA (10:1), Rf 0.52.

Intermediate 92

4-Fluoro N'-[4-fluorophenyl]-1,2-benzendiamine

A solution of potassium carbonate (8.292 g) and sodium hydrosulfite (6.964 g) in water (200 ml) was added to a suspension of the intermediate 91 (2.502 g) in 95% ethanol (350 ml). The mixture was stirred at 23° for 1 h, the reaction mixture was acidified to pH=3.5 with conc. hydrochloric acid and concentrated in vacuo to half volume. A 10% solution of sodium hydroxide was added until pH=10 and the solution was extracted with ethyl acetate (200 ml). The combined organic extracts were washed with brine (200 ml), dried and concentrated in vacuo to give the crude compound (2.93 g) which was purified by flash chromatography using CH-EA 3/2 as eluent to give the title compound as a brown oil (1.64 g). M.p.83°–84°. T.l.c. CH-EA (2:1), Rf 0.35.

Intermediate 93

N'-(Adamantane-1-methyl)-4-Fluoro-N''-(4-fluorophenyl)-1,2-benzendiamine

To a solution of 1-adamantanecarboxaldehyde (1.223 g) and intermediate 92 (1.64 g) in ethanol (50 ml) a buffer prepared with sodium acetate trihydrate (3.04 g) and glacial acetic acid (004 ml) in water (25 ml) was added and the mixture was stirred at 23°. A further amount of ethanol (1 5 ml) was added to get a clear solution and sodium borohydride (2.8 g) was added portionwise. The mixture was stirred at 23° for 20 h, and then diluted with ethyl acetate (30 ml). The combined organic extracts were washed with potassium carbonate (30 ml) with brine (30 ml), dried and concentrated in vacuo to give a red oil (3.102 g) which was purified by flash chromatography (eluting with CH-EA 15:1 to give the title compound as an orange oil (0.854 g). T.l.c. CH-EA (9:1), Rf 0.59.

Intermediate 94

1-(Adamantane-1-methyl)-2,4-Dioxo-7-fluoro-5-(4-fluorophenyl)-3-phenylhydrazono-2,3,4,5-tetrahydro-1H-1,5-benzodiazepine.

The intermediate 93 (0.850 g) and the phenylhydrazonomalonyldichloride (0.565 g) were each taken up in THF (30 ml) and dropped in a flask containing THF (30 ml) maintained under a nitrogen atmosphere. After complete addition the solution was heated to 70 C. for 3 h. The solution was diluted with EA (1 00 ml), washed with 5% sodium hydrogen carbonate solution (100 ml) and brine (100 ml), dried and concentrated in vacuo to a red foam (1.268 g), which was purified by flash chromatography (eluting with CH-EA 3:1) to give the title compound as a yellow foam (0.562 g). T.l.c. CH-EA (3:1), Rf 0.46.

Intermediate 95

1-(Adamantane-1-methyl)-3-Amino-2,4-dioxo-7-fluoro-5-(4-fluoro phenyl)-2,3,4,5-tetrahydro-1H-1,5-benzodiazepine Zinc dust (0.673 g) was added to a solution of the intermediate 94 (0.557 g) in glacial acetic acid (20 ml). The mixture was stirred at 23 C. for 6 h, filtered and evaporated to dryness; the residue was dissolved in water (80 ml), the solution was basified with solid sodium hydroxide until ph=9, extracted with with EA (100 ml). The combined organic extracts were washed with brine (2×30 ml), dried and concentrated in vacuo to give a yellow foam (0.547 g) which was purified by flash chromatography (eluting with EA-Methanol 9/1 to give the title compound as a white solid (0.322 g) M.p. 232°–3°. T.l.c. EA-methanol (9:1), Rf 0.56.

Intermediate 96

N-1-(Adamantane-1-methyl)-3-amino-5-phenyl-2,3,4,5-tetrahydro-1H-1,5-benzodiazepine, (IR)-(–)-10-camphorsulphonate A solution of (IR)-(–)-10-camphorsulphonic acid (13.2 g) in acetonitrile (1035 ml) was added dropwise to a solution of intermediate 41 (33 g) in acetonitrile (1089 ml) and the stirred mixture was left overnight at room temperature. The precipitate was filtered and washed with acetonitrile, (80 ml) ethyl acetate (50 ml) and petroleum ether (50 ml) to give, after drying in vacuum, the title compound (16.17 g) as a white solid. M.P. 270°–2°.

Intermediate 97

(+)N-1-(Adamantane-1-methyl)-3-amino-2,4-dioxo-5-phenyl-2,3,4,5-tetrahydro-1H-1,5-benzodiazepine A suspension of intermediate 96 (6.05 g) in ethyl acetate (395 ml) was mixed with 5% aqueous ammonia (395 ml) for 5 min, and the organic layer separated. The aqueous layer was washed with ethyl acetate (395 ml) and then the ethyl acetate phase separated. The combined organic extracts were dried and the solvent evaporated to give the title compound as a white foam (4.1 g ). T.l.c. EA-methanol (95.5), Rf 0.33 $[alpha]_D$=+31.

Intermediate 98

4-Fluoro-N'-(3-methylbut-1-yl)-N"-phenyl-1,2-benzendiamine

Bromo 3-methylbutane (0.38 ml) was added to a solution of the 5-fluoro N'-phenyl-1,2-benzendiamine (0.645 g) and sodium iodide (0.476 g) in dimethylformamide (25 ml) under a nitrogen atmosphere. The solution was stirred at 120° for 10 h, then cooled to room temperature, diluted with water (30 ml) and extracted with ethyl ether (2×25 ml). The combined organic extracts were washed with brine (30 ml), dried and concentrated in vacuo to give a red oil, which was purified by flash chromatography (eluting with CH-EA 9:1) to give the title compound as a brown oil (0.467 g). T.l.c. CH-EA (2:1), Rf 0.78.

Intermediate 99

2,4-Dioxo-7-fluoro-1-(3-methylbut-1-yl)-5-phenyl-3-phenylhydrazono-2,3,4,5-tetrahydro-1H-1,5-benzodiazepine.

The intermediate 98 (0.454 g) and the phenylhydrazonomalonyldichloride (0.49 g) were each taken up in THF (15 ml) and dropped in a flask containing THF (15 ml) maintained under a nitrogen atmosphere. After complete addition the solution was heated to 70° for 1 h. The solution was diluted with EA (20 ml), washed with 5% sodium hydrogen carbonate solution (20 ml) and brine (20 ml), dried and concentrated in vacuo to an oil, which was purified by flash chromatography (eluting with CH-EA 8:2) to give the title compound as a yellow foam (0.565 g). T.l.c. CH-EA (4:1), Rf 0.33.

Intermediate 100

3-Amino-2,4-dioxo-7-fluoro-1-(3-methylbut-1-yl)-5-phenyl-2,3,4,5-tetrahydro-1H-1,5-benzodiazepine Zinc dust (0.822 g) was added to a solution of the intermediate 99 (0.559 g) in glacial acetic acid (20 ml). The mixture was stirred at 23° for 2 h, then diluted with 10% solution of sodium hydroxide until pH=9 and the mixture extracted with ethyl acetate (2×30 ml). The combined organic extracts were washed with brine (30 ml), dried and concentrated in vacuo to give a brown oil (0.529 g) which was purified by flash chromatography (eluting with CH-Methanol 19/1 to give the title compound as a yellow foam (0.323 g). M.p. 125–6 C. T.l.c. EA-methanol (19:1), Rf 0.45.

EXAMPLE 1

N-[2,4-Dioxo-5-(2-fluorophenyl)-1-(3-methylbut-1-yl)2,3,4,5-tetrahydro-1H-1,5-benzodiazepin-3-yl]-N'-phenylurea Phenyl isocyanate (0.136 ml) was added to a solution of the intermediate 3 (0.4 g) in dry acetonitrile (10 ml) under a nitrogen atmosphere. The mixture was stirred at 23° for 1 h, filtered and the solid washed with diethyl ether to give the title compound as a white solid (0.45 g). M.p. 254–50. T.l.c. CH-EA(1:1), Rf 0.65. IR: 3450 (NH), 1707 and 1670 (C═O), 1601 and 1533 (C═C) cm−1; $^1$H-NMR: 7.459 (dd); 7.4–7.1 (m); 7.03 (m); 6.989 (dd); 6.933 (bs); 6.353 (d); 5.366 (d); 4.457 (m); 3.70 (m); 1.6–1.4 (m); 0.902 (d); 0.888 (d).

EXAMPLE 2

N-[1-(3,3-Dimethylbut-1-yl)-2,4-dioxo-5-(2-fluorophenyl)-2,3,4,5-tetrahydro-1H-1,5-benzodiazepin-3-yl]-N'-phenylurea Phenyl isocyanate (0.106 ml) was added to a solution of the intermediate 6 (0.3 g) in dry acetonitrile (5 ml) under a nitrogen atmosphere. The mixture was stirred at 23° for 1 h, filtered and the solid washed with diethyl ether to give the title compound as a white solid (0.27 g). M.p. 271°–2°. T.l.c. CH-EA (7:3), Rf 0.32. IR: 3310 (NH), 1718, 1668 and 1639 (C═O), 1601 and 1556 (C═C) cm−1; $^1$H-NMR: 7.45 (dd); 7.4–7.10 (m); 7.06–6.97 (m); 6.414 (d); 5.362 (d); 4.476–4.373 (m); 3.757–3.656 (m); 1.503 (m); 0.924 (s).

EXAMPLE 3

N-[2,4-Dioxo-5-(2-fluorophenyl)-1-(3-methylbut-1-yl)-2,3,4,5-tetrahydro-1H-1,5-benzodiazepin-3-yl]-N'-(3-methylmercapto)phenylurea 3-Methylmercaptoaniline (0.065 ml) was added to a solution of the intermediate 7 (0.2 g) in dichloromethane (10 ml) under a nitrogen atmosphere. The solution was stirred at 23° for 3 h, then concentrated in vacuo and triturated with acetonitrile to give the title compound as a white solid (0.132 g). M.p. 246°–7°. T.l.c. CH-EA (1:1), Rf 0.58. IR: 1711,1691,1680 and 1670 (C═O), 1595 (C═C) cm−1; $^1$H-NMR: 7.46 (dd); 7.4–7.3 (m); 7.26–7.10 (m); 7.04–6.9 (m); 6.82–6.76 (bm); 6.257 (d); 5.333 (d); 4.46 (m); 3.700 (m); 2.436 (s); 1.6–1.4 (m); 0.906 (d); 0.886 (d).

EXAMPLE 4

N-[2,4-dioxo-5-(2-fluorophenyl)-1-(3-methylbut-1-yl)-2,3,4,5-tetrahydro-1H-1,5-benzodiazepin-3-yl]-N'-(3-dimethylamino)phenylurea Triethylamine (0.32 ml) and 3-dimethylaminoaniline dihydrochloride (0.24 g) were added to a suspension of the intermediate 8 (0.22 g) in dry dimethylformamide (5 ml) under a nitrogen atmosphere. The resulting mixture was heated to 160° for 2 h, then cooled to room temperature, diluted with water (20 ml) and extracted with ethyl acetate (2×20 ml). The combined organic extracts were dried, concentrated in vacuo and triturated with acetonitrile to give the title compound as a white solid (0.12 g). M.p. 252°–3°. Tlc. CH-EA (1:1), Rf 0.5. IR: 3312 (NH), 1707,1676 and 1639 (C═O), 1593 and 1558 (C═C) cm−1; $^1$H-NMR: 7.45 (dd); 7.41–7.28 (m); 7.25–7.1 (m); 7.134 (t); 6.981 (dd); 6.818 (t); 6.634 (bs); 6.599 (dd); 6.455 (dd); 6.365 (d); 5.359 (d); 4.509–4.409 (m); 3.741–3.645 (m); 2.918 (s); 1.6–1.42 (m); 0.908 (d); 0.896 (d).

EXAMPLE 5

N-[1-(3,3-Dimethylbut-1-yl)-2,4-dioxo-5-(2-fluorophenyl)-2,3,4,5-tetrahydro-1H-1,5-benzodiazepin-3-yl]-N'-(3-methylmercapto)phenylurea 3-Methylmercaptoaniline (0.19 ml) was added to a solution of the intermediate 9 (0.3 g) in dry dimethylformamide (5 ml) under a nitrogen atmosphere. The solution was heated to 160° for 5 h, then cooled to room temperature, diluted with water and extracted with ethyl acetate (2×20 ml). The combined organic extracts were dried, concentrated in vacuo and triturated with acetonitrile to give the title compound as a white solid (0.08 g). M.p. 249°–50°. T.l.c. CH-EA (7:3), Rf 0.33. IR: 3308 (NH), 1707, 1676 and 1643 (C=O), 1607 (C=C) cm−1; $^1$H-NMR: 7.48–7.30 (m); 7.28–7.10 (m); 7.04–6.90 (m); 6.83 (bs); 6.29 (d); 5.34 (d); 4.41 (m); 3.71 (m); 2.44 (s); 1.50 (m); 0.93 (s).

EXAMPLE 6

N-[1-(3,3-Dimethylbut-1-yl)-2,4-dioxo-5-(2-fluorophenyl)-2,3,4,5-tetrahydro-1H-1,5-benzodiazepin.-3-yl]-N'-(3-dimethylamino)phenylurea Triethylamine (0.43 ml) and 3-dimethylaminoaniline dihydrochloride (0.324 g) were added to a solution of the intermediate 9 (0.3 g) in dry dimethylformamide (5 ml) under a nitrogen atmosphere. The solution was heated to 160° for 2 h, then cooled to room temperature, diluted with water and extracted with ethyl acetate (2×20 ml). The combined organic extracts were dried, concentrated in vacuo and triturated with acetonitrile to give the title compound as a white solid (0.16 g). M.p. 255°–6°. T.l.c. CH-EA (6:4), Rf 0.28. IR: 3308 (NH), 1717 (C=O), 1637 (C=C) cm−1; $^1$H-NMR: 7.48–7.10 (m); 6.98 (dd); 6.81 (t); 6.66–6.56 (m); 6.46 (dd); 6.34 (d); 5.36 (d); 4.41 (m); 3.70 (m);

EXAMPLE 7A

N-[1-(3,3-Dimethyl-2-hydroxybut-1-yl)-2,4-dioxo-5-(2-fluorophenyl)-2,3,4,5-tetrahydro-1H-1,5-benzodiazepin-3-yl]-N'-phenylurea Phenyl isocyanate (0.068 ml) was added to a solution of the intermediate 12 (0.28) in dry acetonitrile (5 ml) under a nitrogen atmosphere. The mixture was stirred at 23° for 20 h, concentrated in vacuo and the residue triturated with diethyl ether to give t he title compound as a white solid (0.2 g). M.p. 248°–9°. T.l.c. CH-EA (1:1), Rf 0.60 and 0.58. IR: 3308 (NH), 1709 and 1670 (C=O), 1639 and 1601 (C=C) cm−1; $^1$H-NMR :7.66 (d); 7.46–7.06 (m); 7.02–6.9 (m); 6.8–6.7 (bs); 6.62 (d); 5.412 (d); and 5.402 (d); 4.492 (bd); 4.303 (bm); 3.936 (d); 3.95–3.85 (m); 3.613 (bt); 3.48 (bs); 2.634 (bs); 2.504 (bs); 0.918 (s).

EXAMPLE 7B

N-[1-(3,3-Dimethyl-2-hydroxybut-1-yl)-2,4-dioxo-5-(2-fluorophenyl)-2,3,4,5-tetrahydro-1H-1,5-benzodiazepin-3-yl]-N'-phenylurea (diastereomer I)

Phenyl isocyanate (0.0984 ml) was added to a suspension of the intermediate 13a (0.29 g) in dry acetonitrile (5 ml) under a nitrogen atmosphere. The mixture was stirred at 23° for 20 h, concentrated in vacuo and the residue triturated with diethyl ether to give the title compound as a white solid (0.29 g). M.p. 255°–6° (dec). T.l.c. CH-EA (1:1), Rf 0.6. IR: 3352, 3282 and 3253 (NH and OH), 1705 and 1680 (C=O), 1630 and 1599 (C=C) cm−1; $^1$H-NMR: 7.905 (dd); 7,38–7.24 (m); 7.24–7.1 (m); 7.05 (bs); 6.98–6.85 (m); 6.80 (bs); 5.395 (d); 4.513 (bd); 3.936 (bs); 3.598 (bt); 2.521 (bs); 0.924 (s).

EXAMPLE 7C

N-[1-(3,3-Dimethyl-2-hydroxybut-1-yl)-2,4-dioxo-5-(2-fluorophenyl)-2,3,4,5-tetrahydro-1H-1,5-benzodiazepin-3-yl]-N'-phenylurea (diastereomer II)

Phenyl isocyanate (0.12 ml) was added to a suspension of the intermediate 13b (0.33 g) in dry acetonitrile (5 ml) under a nitrogen atmosphere. The mixture was stirred at 23° for 3 h, filtered and the solid washed with diethyl ether to give the title compound a s a white solid (0.27 g). M.p. 204°–5°. T.l.c. CH-EA (1:1), Rf 0.58. IR: 3308 (NH and OH), 1718 and 1670 (C=O), 1601 (C=C) cm−1; $^1$H-NMR: 7.86 (d); 7.4–7.12 (m); 7.02–6.94 (m); 6.577 (d); 5.414 (d); 4.312 (t); 3.931 (d); 3.454 (bs); 2.560 (bs); 0.919 (s).

EXAMPLE 8

N-[1-(1,3-Dimethylbut-1-yl)-2,4-dioxo-5-phenyl-2,3,4,5-tetrahydro-1H-1,5-benzodiazepin-3-yl]-N'-phenylurea Phenyl isocyanate (0.1 ml) was added to a solution of the intermediate 16 (0.22 g) in dry acetonitrile (10 ml) under a nitrogen atmosphere. The mixture was stirred at 23° for 1 h, concentrated in vacuo to give an oil which was purified by flash chromatography (eluting with CH-EA 80:20 to give a crude sample which was triturated with 1/1 mixture of petroleum/ethyl ether (30 ml) to give the title compound (0.12 g). T.l.c. CH-EA(1:1), Rf 0.53. IR: 3370 (NH), 1701 and 1670 (C=O), 1651 and 1601 (C=C) cm−1; $^1$H-NMR: 7.44–7.35 (m); 7.34–7.24 (m); 7.24–7.15 (m); 6.982 (m); 6.538 (d); 6.529 (d); 5.328 (d); 5.321(d); 4.576 (m); 4.438(q); 2.11(m); 1.74–1.64(m); 1.64–1.44(m); 1.542 (d); 1.435(d); 0.886 (d); 0.882 (d); 0.873 (d); 0.827(d).

EXAMPLE 9

N-[7-Chloro-2,4-dioxo-1-(3-methylbut-1-yl)-5-phenyl-2,3,4,5-tetrahydro-1H-1,5-benzodiazepin-3-yl]-N'-phenylurea Phenyl isocyanate (0.1 ml) was added to a solution of the intermediate 20 (0.2 g) in dry acetonitrile (9 ml) under a nitrogen atmosphere. The mixture was stirred at 0° for 2 h, filtered and the solid triturated with petroleum ether/ethyl ether (2/2 ml) at 0° C., filtered off, washed with 1/1 mixture petroleum ether/ethyl ether (10 ml ) to give the title compound as a white solid (0.17 g). T.l.c. CH-EA(1:1), Rf 0.59. IR: 3312 (NH), 1713 and 1684 (C=O), 1639 and 1605 (C=C) cm−1; $^1$H-NMR: 7.45–7.00 (m); 7.10(m); 6.989 (dd); 6.97 (d); 6.42 (d); 5.31 (d); 4.51(m); 3.59 (m); 1.58–1.46 (m); 1.46–1.38(m); 0.87 (d); 0.85(d).

EXAMPLE 10

N-[8-Chloro-2,4-dioxo-1-(3-methylbut-1-yl)-5-phenyl-2,3,4,5-tetrahydro-1H-1,5-benzodiazepin-3-yl]-N'-phenylurea Phenyl isocyanate (0.1 ml) was added to a solution of the intermediate 25 (0.2 g) in dry acetonitrile (4 ml) under a nitrogen atmosphere. The mixture was stirred at 0° for 30 min, then petroleum ether was added and stirring was continued for 1 h. the solid was filtered off, washed with 3/1 mixture petroleum ether/ethyl ether (15 ml ) to give the title compound as a white solid (0.22 g). T.l.c. CH-EA (1:1), Rf 0.63. IR: 3310 (NH), 1717,1668 and 1641 (C=O), cm−1; $^1$H-NMR: 7.44–7.35 (m); 7.32(t); 7.25–7.16 (m); 7.14 (m); 7.03 (m); 6.92 (m); 6.41(d); 5.31 (d); 4.52(m); 3.62(m); 1.60–1.40 (m); 0.89(d); 0.87(d).

EXAMPLE 11

N-[7,8-dichloro-2,4-Dioxo-1-(3-methylbut-1-yl)-5-phenyl-2,3,4,5-tetrahydro-1H-1,5-benzodiazepin-3-yl]-N'-phenylurea Phenyl isocyanate (0.09 ml) was added to a solution of the intermediate 30 (0.19 g) in dry acetonitrile (2.5 ml) under a nitrogen atmosphere. The mixture was stirred at 0° for 20 min, then evaporated to dryness and the resulting solid solid triturated with 1/1 mixture petroleum ether/ethyl ether (10 ml) at 0° C. for 1 h, filtered off, washed with 1/1 mixture petroleum ether/ethyl ether (15 ml) to give the title compound as a white solid (0.15 g). T.l.c. CH-EA (1:1), Rf 0.6. IR: 3375 (NH), 1711,1684 and 1655 (C=O), 1 599, 1547 9 C=C) cm−1; $^1$H-NMR: 7.51 (s); 7.46–7.32(m); 7.28–7.14 (m); 7.05 (s); 7.06–7.00 (m); 6.40 (d); 5.31 (d); 4.50m); 3.56(m); 1.60–1.40 (m); 0.89(d); 0.86(d).

EXAMPLE 12

N-[2,4-Dioxo-8-Fluoro-1-(3-methylbut-1-yl)-5-phenyl-2,3,4,5-tetrahydro-1H-1,5-benzodiazepin-3-yl]-N'-phenylurea Phenyl isocyanate (0.1 ml) was added to a solution of the intermediate 35 (0.2 g) in dry acetonitrile (2.5 ml) under a nitrogen atmosphere. The mixture was stirred at 0° for 30 min, then diethyl ether (5 ml) was added and stirring continued for 1 h. The resulting solid was filtered off, washed with 1/1 mixture petroleum ether/ethyl ether (10 ml) to give the title compound as a white solid (0.25 g). Tlc. CH-EA(1:1), Rf 0.53. IR 3312 (NH), 1718,1670(C=O), 1639, 1605(C=C) cm−1; $^1$H-NMR: 7.44–7.36 (m); 7.32(t); 7.30–7.10(m); 7.06–6.9 (m); 6.35(d); 5.33 (d); 4.52(m); 3.62(m); 1.60–1.40 (m); 0.90(d); 0.87(d).

EXAMPLE 13

N-[-2,4-Dioxo-5-phenyl-1-(2-phenylethyl)-2,3,4,5-tetrahydro-1H-1,5-benzodiazepin-3-yl]-N'-phenylurea Phenyl isocyanate (0.1 ml) was added to a solution of the intermediate 38 (0.3 g) in dry acetonitrile (15 ml) under a nitrogen atmosphere. The mixture was stirred at 23° for 1 h, EE (30 ml) was added and the formed precipitate was stirred for 45 min at 0°. The precipitate was filtered, washed with diethyl ether (25 ml) to give the title compound as a white solid (0.27 g). T.l.c. CH-EA (1:1), $R_f$=0.45. IR: 3310 (NH), 1707, 1678 (C=O); 1643, 1603, 1556 (C=C) cm−1; $^1$H-NMR: 7.428 (dd), 7.36–7.27 (m), 7.27–7.12 (m), 7.07–6.94 (m), 6.484 (d), 5.361 (d), 4.78–4.66 (m), 3.98–3.86 (m), 2.927 (m).

EXAMPLE 14

N-[1-(1-Adamantyl)methyl-2,4-dioxo-5-phenyl-2,3,4,5-tetrahydro-1H-1,5-benzodiazepin-3-yl]-N'-phenylurea Phenyl isocyanate (0.039 ml) was added to a solution of the intermediate 41 (0.13 g) in dry acetonitrile (7 ml) under a nitrogen atmosphere. The mixture was stirred for 1.5 hrs and the formed precipitate was filtered washing with acetonitrile (3 ml) to give the title compound as a white solid (0.085 g). T.l.c. CH-EA (1:1), $R_f$=0.23. IR: 3294 (NH), 1717, 1705, 1680 (C=O); 1643 (C=C) cm−1; $^1$H-NMR: 7.5–6.96 (m), 7.08 (bs), 6.50 (d), 5.31 (d), 4.49 (d), 3.37 (d), 1.84 (m), 1.6–1.3 (m).

EXAMPLE 15

N-[1-(2,2-Dimethylethoxycarbonylmethyl)-2,4;dioxo-5-phenyl-2,3,4,5-tetrahydro-1H-1,5-benzodiazepin-3-yl]-N'-phenylurea Phenyl isocyanate (0.09 ml) was added to a solution of the intermediate 44 (0.244 g) in dry acetonitrile (16 ml) under a nitrogen atmosphere. The mixture was stirred at 23° for 2 h, dichloromethane (30 ml) was added and the organic layer was washed with brine (2×10 ml), dried and concentrated "in vacuo". The crude product was purified by flash chromatography (eluting with DCM-methanol 98:2), to give the title compound as a white solid (0.232 g). T.l.c. DCM-methanol (95:5), $R_f$=0.8. IR: 343 1, 3395 (NH), 1745, 1684 (C=O) cm−1; $^1$H-NMR: 7.4–6.95 (m), 7.1 (bs), 6.5 (d), 5.45 (d), 4.61 (dd), 1.40 (s).

EXAMPLE 16

N-[1-(3,3-Dimethylbutyl)-2,4-dioxo-5-phenyl-2,3,4,5-tetrahydro-1H-1,5-benzodiazepin-3-yl]-N'-phenylurea Phenyl isocyanate (0.067 ml) was added to a solution of the intermediate 47 (0.190 g) in dry acetonitrile (10 ml) under a nitrogen atmosphere. The mixture was stirred at 23° for 1 h and the formed precipitate was filtered washing with acetonitrile (3 ml), to give the title compound as a white solid (0.198 g). T.l.c. CH-EA (1:1), $R_f$=0.57. IR: 3431, 3350 (NH), 1745, 1668 (C=O) 1599 (C=C) cm−1; $^1$H-NMR: 7.48–7.26 (m), 7.26–7.14 (m), 7.04–6.96 (m), 6.523 (d), 5.352 (d), 4.511–4.409 (m), 1.467 (t), 0.915 (s).

EXAMPLE 17

N-[2,4-Dioxo-1-(2-hydroxy-3-methylbutyl)-5-phenyl-2,3,4,5-tetrahydro-1H-1,5-benzodiazepin-3-yl]-N'-phenylurea To a solution of intermediate 63 (0.12 g) in methanol (20 ml) and water (3 ml), sodium borohydride (1.5 g) was added portionwise at 0°, maintaining the pH at 7–7.5 by adding a 1M solution of hydrochloric acid. During the reaction, further methanol was added. The reaction mixture was stirred for 1 hr, then concentrated, diluted with ethyl acetate (100 ml) and washed with brine (3×70 ml), dried and concentrated "in vacuo". The crude product was dissolved in diethyl ether (5 ml) and precipitated with petroleum ether (10 ml), to give the title compound as a white solid (0.07 g). T.l.c. CH-EA (1:1), $R_f$=0.36. IR: 3337 (NH, OH), 1701, 1647 (C=O); 1597, 1553 (C=C) cm−1; $^1$H-NMR: 7.6–6.65 (m), 5.37 (d), 5.35 (d), 3.92 (bm), 3.48 (bm), 4.50 (dd), 3.80 (dd), 4.34 (dd), 3.57 (dd), 2.50 (bm), 1.58 (m), 0.93–0.87 (m).

EXAMPLE 18

N-[1-(3,3-Dimethylbutyl)-2,4-dioxo-5-phenyl-2,3,4,5-tetrahydro-1H-1,5,benzodiazepin-3-yl]-N'-(3-trifluoromethoxyphenyl)urea A solution of 3-trifluoromethoxyphenylamine (0.047 g) and intermediate 48 (0.100 g) in dichloromethane (5 ml) were stirred for 20 h at 23° under a nitrogen atmosphere, then concentrated "in vacuo". The crude product was triturated with acetonitrile (2 ml) to obtain the title compound as a white solid (0.067 g). T.l.c. CH-EA (60:40), R$_f$=0.57. IR: 3317 (NH), 1717, 1650 (C=O); 1609, 1558 (C=C) cm$^{-1}$; $^1$H-NMR: 7.53 (bs), 7.46 (dd), 7.45–7.30 (m), 7.30–7.18 (m), 7.10 (t), 7.00 (dd), 6.88 (m), 6.77 (m), 6.66 (d), 5.35 (d), 4.44 (m), 3.70 (m), 1.54–1.42 (m), 0.91 (s).

EXAMPLE 19

N-[1-(3,3-Dimethylbutyl)-2,4-dioxo-5-phenyl-2,3,4,5-tetrahydro-1H-1,5-benzodiazepin-3-yl]-N'-(3-cyanophenyl)urea A solution of 3-cyanophenylamine (0.118 g) and intermediate 48 (0.339 g) in dichloromethane (10 ml) were stirred for 5 h at 23° under a nitrogen atmosphere, then concentrated "in vacuo". The crude product was triturated with acetonitrile (8 ml), filtered and washed with acetonitrile (3 ml) to obtain the title compound as a white solid (0.216 g). T.l.c. CH-EA (1:1), R$_f$=0.55. IR: 3319 (NH), 2230 (C=N), 1711, 1647 (C=O); cm$^{-1}$; $^1$H-NMR: 7.91 (bs); 7.52–7.30 (m), 7.30–7.12 (m), 7.01 (dd), 6.88 (d), 5.34 (d), 4.52–4.38 (m), 3.80–3.68 (m), 1.51 (m), 0.91 (s).

EXAMPLE 20

N-[1-(3,3-Dimethylbutyl)-2,4-dioxo-5-phenyl-2,3,4,5-tetrahydro-1H-1,5-benzodiazepin-3-yl]-N'-(3-methylthiophenyl)urea To a solution of the intermediate 49 (0.20 g) in dry DMF (5 ml), 3-methylthiophenylamine (0.218 ml) was added and the reaction mixture was stirred for 4 h at 120°, under a nitrogen atmosphere. Ethyl acetate (50 ml) added and the solution washed with water (2×25 ml), and brine (25 ml), dried and concentrated "in vacuo". The crude product was triturated with acetonitrile (4 ml) to obtain the title compound as a white solid (0.115 g). T.l.c. CH-EA (1:1), R$_f$=0.62. IR: 3300 (NH), 1705, 1674, 1641 (C=O); 1607 (C=C) cm$^{-1}$; $^1$H-NMR: 7.48–7.10 (m), 7.02–6.90 (m), 6.82 (s), 6.30 (d), 5.30 (d), 4.46 (m), 3.70 (m); 2.44 (s), 1.48 (t), 0.93 (s).

EXAMPLE 21

N-[1-(3,3-Dimethylbutyl)-2,4-dioxo-5-phenyl-2,3,4,5-tetrahydro-1H-1,5-benzodiazepin-3-yl]-N'-(3-N,N-dimethylaminophenyl)urea To a solution of the intermediate 49 (0.20 g) in dry DMF (8 ml), 3-N,N-dimethylaminophenylamine hydrochloride (0.177 g) and triethylamine (0.118 ml) were added and the reaction mixture was stirred for 4 h at 120°, under a nitrogen atmosphere. Ethyl acetate (50 ml) added and the solution washed with water (2×25 ml) and brine (25 ml), dried and concentrated "in vacuo". The crude product was purified by flash chromatography (eluting with CH-EA 60:40), then triturated with a mixture of ethyl acetate and petroleum ether to obtain the title compound as a white solid (0.076 g). T.l.c. CH-EA (1:1), R$_f$=0.31. IR: 3500 (NH), 1794, 1707, 1666 (C=O); 1607 (C=C) cm$^{-1}$; $^1$H-NMR: 7.46–7.10 (m), 6.99 (dd), 6.82 (t), 6.60 (m), 6.46 (m), 6.53 (bs), 6.31 (d), 5.31 (d), 4.47 (m), 3.69 (m), 2.94 (s), 2.93 (s), 1.47 (m), 0.94 (s).

EXAMPLE 22

N-[1-[2-(1-Adamantyl)ethyl]-2,4-dioxo-5-phenyl-2,3,4,5-tetrahydro-1H-1,5-benzodiazepin-3-yl]-N'-(3-N,N-dimethylaminophenyl)urea To a solution of the intermediate 50 (0.12 g) in dry DMF (2 ml), 3-N,N-dimethylaminophenylamine dihydrochloride (0.084 g) and triethylamine (0.1 ml) were added and the reaction mixture was stirred for 9 h at 120°, under a nitrogen atmosphere. Ethyl acetate (50 ml) added and the solution washed with a saturated solution of ammonium chloride (50 ml) and brine (3×50 ml), dried and concentrated "in vacuo". The crude product was triturated with acetonitrile (10 ml) to obtain the title compound as a white solid (0.030 g). T.l.c. CH-EA (1:1), R$_f$=0.37. IR: 3373 CNH), 1707, 1682, 1660 (C=O); 1595 1580 (C=C) cm$^{-1}$; $^1$H-NMR: 7.45–6.35 (m), 7.34–7.26 (m), 7.22–7.15 (m), 7.116 (t), 6.978 (dd), 6.740 (bs), 6.563 (dd), 6.44 (dd), 6.418 (d), 5.314 (d), 4.523–4.420 (m), 3.721–3.621 (m), 2.911 (s), 1.936 (bs), 1.672 (bq), 1.500 (d), 1.332 (t).

EXAMPLE 23

N-[1-(2,3-Dimethyl)butyl-2,4,-dioxo-5-phenyl-2,3,4,5-tetrahydro-1H-1,5-benzodiazepin-3-yl]-N'-phenylurea Phenyl isocyanate (0.03 ml) was added to a solution of the intermediate 56 (0.087 g) in dry acetonitrile (3 ml), at 0°, under a nitrogen atmosphere. The mixture was allowed to stand at 23° and stirred for 1 h, then petroleum ether was added and the formed precipitate was stirred for 4 h, filtered and washed with petroleum ether. The precipitate was triturated with a mixture petroleum-ether/diethyl ether (1:1; 10 ml) for 1 hr and filtered to give the title compound as a white solid (0.08 g). T.l.c. CH-EA (1:1 ), R$_f$=0.49. IR: 3300 (NH), 1707, 1641 (C=O); 1558, 1541 (C=C) cm$^{-1}$; $^1$H-NMR: 7.46–7.10 (m), 6.9 (m), 6.4 (m), 5.32 (d), 5.29 (d), 4.61 (dd), 4.48 (dd), 3.60 (dd), 3.42 (dd), 1.8 (m), 1.4 (m), 0.86 (d), 0.80 (d), 0.77 (d), 0.75 (d), 0.73 (d), 0.70 (d).

EXAMPLE 24

N-[1-Butyl-2,4-dioxo-5-phenyl-2,3,4,5-tetrahydro-1H-1,5-benzodiazepin-3-yl]N'-phenylurea Phenyl isocyante (0.04 ml) was added to a solution of the intermediate 59 (0.09 g) in dry acetonitrile (10 ml), at 23°, under a nitrogen atmosphere. The mixture was stirred for 3 h, dichloromethane (30 ml) added and the solution washed with water (50 ml), purified by filtration on a pad of silica (eluting with DCM), to give the title compound as a white solid (0.1 g). T.l.c. DCM-methanol (95:5), R$_f$=0.65. IR: 3431 (NH), 1707, 1670 (C=O); 1599 (C=C) cm-1; $^1$H-NMR: 7.4–7.00 (m), 6.66 (bs), 6.22 (d), 5.3 (d), 4.55 (m), 3.7 (m), 1.53 (m), 1.3 (m), 0.88 (t).

EXAMPLE 25

N-[2,4-Dioxo-5-phenyl-1-(3-methylbut-1-yl)-2,3,4,5-tetrahydro-1H-1,5-benzodiazepin-3-yl]-N'-phenylurea Phenyl isocyanate (0.08 ml) was added to a solution of intermediate 66 (0.206 g) in dry acetonitrile (12 ml) under a nitrogen atmosphere. The mixture was stirred at 23° for 1 h, then dichloromethane was added until complete dissolution of the precipitate. The organic layer was separated, washed with brine (3×20 ml) dried and concentrated in vacuo to give the crude compound (0.3 g) which was purified by flash chromatography (eluting with DCM-methanol 98:2) to give the title compound as a white solid (0.06 g). T.l.c. DCM-methanol (95:5), Rf 0.87. IR: 3440–3350 (NH), 1701 and 1680 (C=O), 1616 and 1599 (C=C) cm−1; $^1$H-NMR: 7.44–7.16 (m); 7.00 (m); 6.4(m); 5.33(d); 4.53(m); 3.68 (m); 1.6–1.4 (m); 0.89 (d); 0.86(d).

EXAMPLE 26

(+)-N-[2,4-Dioxo-5-phenyl-1-(3-methylbut-1-yl)-2,3,4,5-tetrahydro-1H-1,5-benzodiazepin-3-yl]-N'-phenylurea Phenyl isocyanate (0.15 ml) was added to a solution of intermediate 70 (0.42 g) in dry acetonitrile (20 ml) under a nitrogen atmosphere. The mixture was stirred at 23° for 1 h, then the precipitate was filtered off and washed with acetonitrile (10 ml) and dried to give the title compound as a white solid (0.52 g). [alpha]$_D$=+116. T.l.c. DCM-methanol (95:5), Rf 0.87. IR: 3308 (NH); 1703–1674 (C=O), 1645 and 1601(C=C) cm−1; $^1$H-NMR: 7.5–7.1 (m); 6.98 (m); 6.58(d); 5.34(d); 4.53(m); 3.68 (m); 1.58–1.4 (m); 0.87 (d); 0.84(d).

EXAMPLE 27

(+)-N-[2,4-Dioxo-5-(2-fluorophenyl)-1-(3-methylbut-1-yl)-2,3,4, 5-tetrahydro-1H-1,5-benzodiazepin-3-yl]-N'-[3-(N,N-dimethylamino)phenyl]urea 3-(N,N-Dimethylamino)phenyl isocyanate) (0.257 g) was added to a solution of the intermediate 72 (0.47 g) in dry acetonitrile (10 ml) under a nitrogen atmosphere. The reaction mixture was stirred at 23° for 1 h and the formed precipitate was filtered to give the title compound as a white solid (0.58 g) in enantiomeric ratio (+)/(−)=93/7. A sample was purified by HPLC to give the pure title compound. M.p. 252-3. T.l.c. CH-EA (1:1), Rf 0.50. [alpha]D=+109.6. IR (nujol):3420 (NH), 1717,1701,1690 and 1649 (C=O), 1616 and 1560 (C=C) cm−1: 1H-NMR: 7.45 (dd); 7.42–7.28 (m); 7.25–7.1 (m); 6.98 (dd); 6.82 (t); 6.60 (m); 6.45 (dd); 6.356 (d); 5.36 (d); 4.52–4.38 (m); 3.80–3.60 (m); 2.92 (s); 1.66–1.4 (m); 0.90 (d); 0.89 (d).

EXAMPLE 28

N-[1-(Adamant-2-yl)-2,4-dioxo-5-phenyl-2,3,4,5-tetrahydro-1H-1,5-benzodiazepin-3-N'-[3-(N,N-dimethylaminophenyl)]urea Triethylamine (0.065 ml) and 3-dimethylaminoaniline dihydrochloride (0.049 g) were added to a solution of the intermediate76 (0.1 g) in dichloromethane (5 ml) under a nitrogen atmosphere. The solution was stirred at 23 for 3 h, then concentrated in vacuo and purified by flash chromatography (eluting with CH-EA 1:1) to give the title compound (0.052 g) as a white solid. T.l.c. DCM-methanol (95:0.5), Rf 0.72. IR: 3300 (NH), 1713 and 1676 (C=O), 1637 and 1610 (C=C) cm−1; 1H-NMR:7.4–7.1 (m); 6.99 (m); 6.80 (t); 6.62 (m); 6.56 (dd); 6.45 (dd); 6.31 (d); 5.31 (d); 4.52 (m); 2.91 (m); 2.32 (m); 2.0–1.1 (m).

EXAMPLE 29

N-(2-cyclopentyl-ethyl)-2,4-dioxo-5-(2-fluorophenyl)-2,3,4,5-tetrahydro-1H-1,5-benzodiazepin-3-yl]-N'-phenylurea Phenyl isocyanate (0.044 ml) was added to a solution of the intermediate 79 (0.154 g) in acetonitrile (5 ml) under a nitrogen atmosphere. The mixture was stirred at 23° for 1 h; the obtained solid was filtered and washed with acetonitrile (2 ml) to give the the title compound (0.163 g) as a white solid. Mp 255°–257° T.l.c. CH-EA (1:1), Rf 0.58 . IR: 3400 (NH), 1718 and 1650 (C=O), 1600 (C=C) cm−1; 1H-NMR: 7.46 (dd); 7.4–7.1(m); 7.0(t); 6.98 (d); 6.52 (d);5.38 (d); 4.44(m); 3.66 (m); 1.84–1.40 (m); 1.20–1.0 (m).

EXAMPLE 30

N-[1-(2-cyclopentyl-ethyl)-2,4-dioxo-5-(2-fluoro-phenyl)-2,3,4,5-tetrahydro-1H-1,5-benzodiazepin-3-yl]-N'-[4-(dimethylamino)phenyl]urea Triethylamine (0.184 ml) and 4-(dimethylamino)aniline (0.138 g) were added to a solution of the intermediate 80 (0.270 g) in dry dichloromethane (50 ml) under a nitrogen atmosphere. The solution was stirred at 23° for 4 h, then diluted with dichloromethane (20m 1) and washed with water (20 ml), 5% HCl solution (20 ml), water (20 ml)and brine (15 ml). The organic layer was dried, concentrated in vacuo, and the residue was purified by flash chromatography (eluting with DCM-methanol 95:5) to give the title compound (0.077 g) as a white solid. T.l.c. DCM-methanol (9:1), Rf 0.81. IR: 3304 (NH), 1718–1641 (C=O), 1605–1549 (C=C) cm−1; 1H-NMR: 7.46(dd); 7.40–7.10 (m); 6.98 (dd); 6.68 (d); 6.28 (bs); 6.07 (d); 5.32 (d ); 4.41 (m ); 3.66 (m); 2.91 (s); 1.84–1.00 (m).

EXAMPLE 31

N-[1-(Bicyclo[2.2.1]-5-heptene-2-ylmethyl)-2,4-dioxo-5-phenyl-2,3,4,5-tetrahydro-1H-1,5-benzodiazepin-3-yl]-N'-phenylurea Phenylisocyanate (0.026 ml) was added to a solution of the intermediate 83 (0.074 g) in dry acetonitrile (5 ml) and the mixture was stirred at 23°, under nitrogen, for 1 h. Dichloromethane (50 ml) was added until complete dissolution of the precipitate, then the solution was washed with brine (20 ml), dried and concentrated in vacuo. The residue was triturated with diethyl ether to give the title compound (0.0521 g) as an off-white solid. M.p. 184–6 C. T.l.c. (CH-EA 7:3) R$_f$ 0.32. IR: 3308 (NH), 1715–1670(C=O), 1639–1599 9C=C); 1H-NMR: 7.5–7.0 (m); 6.84 (bs); 6.80 (bs); 6.33(d); 6.31 (d); 6.18–6.10 (m); 6.12–5.96 (m); 5.90–5.84 (m); 5.64–5.60 (m); 5.32 (d); 5.29 (d); 4.64 (m); 4.4–4.2 (m); 3.8 (m); 3.45–3.30 (m); 2.80 (bs); 2.74 (bs); 2.6–0.60 (m).

EXAMPLE 32

N-[1-(Bicyclo[2.2.1]-5-heptene-2-ylmethyl)-2,4-dioxo-5-phenyl-2,3,4,5tetrahydro-1H-1,5-benzodiazepin-3-yl]-N'-(3-nitrophenyl)-urea To a solution of the intermediate 83 (0.072 g) in dry acetonitrile (10 ml) 3-nitrophenylisocyanate (0.048 g) was added and the mixture was stirred at 23°, under nitrogen, for 1 h. The resulting precipitate was filtered, washed with diethyl ether, and dried to give the title compound (0.0712 g). M.p. 195–7 C.

T.l.c. (CH-EA 7:3) R$_f$0.24. IR: 3300 (NH); 1713 (C=O); 1651 (C=O); 1556 (C=C) cm−1. 1H-NMR: 8.26–6.92 (m); 6.13–5.58 (m);5.34–5.25 (m); 4.70–3.83 (m); 2.80–0.45 (m).

EXAMPLE 33

N-[1-(Bicyclo[2.2.1]-2-heptylmethyl)-2,4-dioxo-5-phenyl-2,3,4,5-tetrahydro-1H-1,5-benzodiazepin-3yl]-N'-phenylurea Phenylisocyanate (0.03 ml) was added to a solution of the intermediate 84 (0.088 g) in dry acetonitrile (10 ml) and the mixture was stirred at 23°, under nitrogen, for 1 h. The resulting precipitate was filtered, washed with diethyl ether and dried to give the title compound (0.0858 g) as a white solid. M.p, 255°–6°. T.l.c. (CH-EA 7:3) $R_f$ 0.29. IR: 3400–3200 (NH), 1711 and 1705 (C=C); 1H-NMR: 7.50–7.10 (m),7.02 (m), 6.38 (m), 6.91 (bs), 6.42–6.34 (m), 5.35–5.27(m), 4.71–4.61 (dd), 4.48 (dd), 4.38 (dd), 3.65 (dd), 3.59 (dd) 3.37 (dd), 3.55 (dd), 2.3–0.50 (m).

EXAMPLE 34

N-[1-(Bicyclo[2.2.1]-2-heptylmethyl)-2,4-dioxo-5-phenyl-2,3,4,5-tetrahydro-1H-1,5-benzodiazepin-3yl]-N'-(3-methoxyphenylurea To a solution of the intermediate 84 (0.0883 g) in dry acetonitrile (10 ml) and the mixture was stirred at 23° under nitrogen, for 1 h. The resulting precipitate was filtered, washed with diethyl ether and dried to give the title compound (0.0858 g) as a white solid. M.p. 255°–6°. T.l.c. (CH-EA 7:3) Rf 0.29. IR: 3400–3200(NH), 1711 and 1705 (C=C); $^1$H-NMR: 7.5–6.9(m); 6.75–6.69(m); 6.60–6.55(m); 6.44(m); 5.31(m); 4.71–4.62(m); 4.49(dd) 4.38(dd); 3.75(s); 3.65(dd); 3.59(dd); 3.56(dd); 3.38(dd); 2.25–0.6(m).

Example 35

N-[1-[Bicyclo[2.2.1]-2-heptyl]-2,4-dioxo-5-phenyl-2,3,4,5-tetrahydro-1H-1,5-benzodiazepin-3-yl]-N'-phenylurea Phenyl isocyanate (0.056 ml) was added to a solution of the intermediate 87 (0.15 g) in dry acetonitrile (5 ml) under a nitrogen atmosphere. The mixture was stirred at 23° for 1 h, then filtered. The solid obtained was washed with diethyl ether and dried in vacuo to give the title compound as a white solid (0.12 g). M.p. 267°–8°. T.l.c. CH-EA(1:1), Rf 0.62. IR: 3300 (NH), 1705, 1678 and 1645 (C=O), 1599 and 1556 (C=C) cm–1; $^1$H-NMR: 7.46–7.12 (m); 7.026–6.94 (m); 6.423 (d); 6.436 (d); 5.328 (d); 5.321 (d); 4.5–4.4 (m); 3.459 (s); 2.637 (s); 2.396 (m); 2.180 (m); 1.958 (m); 1.6 (m); 1.54–1.38 (m); 1.3–1.1 (m); 0.99 (m); 0.864 (m).

Example 36

N-[1-(2-Adamantylmethyl)-2,4-dioxo-5-phenyl-2,3,4,5-tetrahydro-1H-1,5-benzodiazepin-3-yl]-N'-phenylurea Phenyl isocyanate (0.063 ml) was added to a solution of the intermediate 90 (0.28) in dry acetonitrile (5 ml) under a nitrogen atmosphere. The mixture was stirred at 23° for 1 h, then filtered. The solid obtained was washed with diethyl ether and dried in vacuo to give the title compound as a white solid (0.22 g). M.p. 192°–3°. T.l.c. CH-EA (1:1), Rf 0.73. IR: 3306 (NH), 1717 and 1701 (C=O), 1643 and 1620 (C=C) cm–1; $^1$H-NMR: 7.5–7.14 (m); 7.00 (m); 7.049 (m); 6.47 (d); 5.33 (d); 5.05 (m); 3.59 (m); 2.02 (m); 1.84–1.36 (m).

EXAMPLE 37

N-[1-(1-Adamantylmethyl)-2,4-dioxo-5-phenyl-2,3,4,5-tetrahydro-1H-1,5-benzodiazepin-3-yl]-N'-(3-methoxyphenyl)urea 3-Methoxyphenyl isocyanate (0.066 ml) was added to a solution of the intermediate 41 (0.2 g) in dry acetonitrile (10 ml) under a nitrogen atmosphere. The mixture was stirred at 23° for 16 h, then diluted with dichloromethane (15 ml) and washed with brine (15 ml). The organic solution was dried, concentrated in vacuo and the residue was purified by flash chromatography (eluting with CH-EA 2:1); the solid obtained was further purified by trituration with diethyl ether to give the title compound as a white solid (0.2 g). M.p. 267°–8°. T.l.c. CH-EA (2:1), Rf 0.2. IR: 3302 (NH), 1713, 1674 and 1641 (C=O), 1612 and 1558 (C=C) cm–1; 1H-NMR: 7.492 (dd); 7.45–7.35 (m); 7.35–7.25 (m); 7.162 (m); 7.120(t); 7.041 (t); 6.992 (dd); 6.904 (s); 6.738(m); 6.578 (m); 6.413 (m); 5.292 (d); 4.496 (d); 3.744 (s); 3.382 (d); 1.857 (s); 1.66–1.32 (m).

EXAMPLE 38

N-[1-(1-Adamantylmethyl)-2,4-dioxo-5-phenyl-2,3,4,5-tetrahydro-1H-1,5-benzodiazepin-3-yl]-N'-(3-methylphenyl)urea 3-Methylphenyl isocyanate (0.064 ml) was added to a solution of the intermediate 41 (0.2 g) in dry acetonitrile (10 ml) under a nitrogen atmosphere. The mixture was stirred at 23° for 1 h, then diluted with dichloromethane (15 ml) and washed with brine (15 ml). The organic solution was dried, concentrated in vacuo and the residue was triturated with diethyl ether to give the title compound as a white solid (0.2 g). M.p. 244°–6°. T.l.c. CH-EA (2:1), Rf 0.32. IR: 3300 (NH), 1715 and 1672 (C=O), 1645 and 1616 (C=C) cm–1; 1H-NMR: 7.493 (dd); 7.45–7.35 (m); 7.35–7.25 (m); 7.21–7.15 (m); 7.135 (t); 7.034 (m); 6.992 (dd); 6.854 (m); 6.751 (s); 6.318 (d); 5.293 (d); 4.498 (d); 3.384 (d); 2.287 (s); 1.865 (s); 1.68–1.3 (m).

EXAMPLE 39

N-[1-(1-Adamantylmethyl)-2,4-dioxo-5-phenyl-2,3,4,5-tetrahydro-1H-1,5-benzodiazepin-3-yl]-N'-(3-nitrophenyl)urea A solution of 3-nitrophenyl isocyanate (0.082 g) in dry acetonitrile (8 ml) was added to a solution of the intermediate 41 (0.2 g) in dry acetonitrile (10 ml) under a nitrogen atmosphere. The mixture was stirred at 23° for 2 h, then diluted with dichloromethane (15 ml) and washed with brine (15 ml). The organic solution was dried, concentrated in vacuo and the residue was triturated with diethyl ether to give the title compound as a white solid (0.229 g). M.p. 213°–5°. T.l.c. CH-EA (2:1), Rf 0.33. IR: 3296 (NH), 1713 and 1645 (C=O), 1597 (C=C) cm–1; 1H-NMR: 8.25 (s); 8.15 (t); 7.64 (m); 7.52 (dd); 7.45 (m); 7.36–7.29 (m); 7.24–7.17 (m); 7.13 (t); 7.06 (d); 7.02 (dd); 5.27 (d); 4.51 (d); 3.40 (d); 1.86 (s); 1.66–1.34 (m).

EXAMPLE 40

N-[1-(1-Adamantylmethyl)-2,4-dioxo-5-phenyl-2,3,4,5-tetrahydro-1H-1,5-benzodiazepin-3-yl]-N'-(3-bromophenyl)urea 3-Bromophenyl isocyanate (0.063 ml) was added to a solution of the intermediate 41 (0.2 g) in dry acetonitrile (10 ml) under a nitrogen atmosphere. The mixture was stirred at 23° for 1h, then filtered. The solid obtained was washed with diethyl ether to give the title compound as a white solid (0.25 g). M.p. 254°–6°T.l.c. CH-EA (2:1), Rf 0.53. IR: 3290 (NH), 1717 and 1672 (C=O) cm–1; 1H-NMR: 7.56–7.15 (m); 7.03–6.88 (m); 6.99 (dd); 6.93 (dd); 6.73 (d); 5.29 (d); 4.49–3.38 (m); 1.83 (m); 1.64–1.30 (m).

EXAMPLE 41

N-[1-(1-Adamantylmethyl)-2,4-dioxo-5-phenyl-2,3,4,5-tetrahydro-1H-1,5-benzodiazepin-3-yl]-N'-(3-ethoxycarbonylphenyl)urea 3-Nitrophenyl isocyanate (0.1 g) was added to a solution of the intermediate 41 (0.415 g) in dry acetonitrile (13 ml) under a nitrogen atmosphere. The mixture was stirred at 23° for 1 h, then diluted with dichloromethane (20 ml) and washed with brine (20 ml). The organic solution was dried, concentrated in vacuo and the residue was triturated with diethyl ether to give the title compound as a white solid (0.407 g). M.p. 246–80. T.l.c. CH-EA (2:1), Rf 0.37. IR: 1709, 1690 and 1670 (C=O) cm–1; 1H-NMR: 7.93 (t); 7.64–7.50 (m); 7.44–7.39 (m); 7.38 (s); 7.35–7.27 (m); 7.24–7.14 (m); 6.89 (dd); 6.58 (d); 5.31 (d); 4.50 (d); 4.34 (m); 3.38 (d); 1.85 (m); 1.61–1.51 (m); 1.45–1.37 (m); 1.35 (t).

EXAMPLE 42

N-[1-(1-Adamantylmethyl)-2,4-dioxo-5-phenyl-2,3,4,5-tetrahydro-1H-1,5-benzodiazepin-3-yl]-N'-[3-(N,N-dimethylamino)phenyl]urea A solution of 3-(N,N-dimethylamino)phenyl isocyanate (0.122 g) in dry acetonitrile (7 ml) was added to a solution of the intermediate 41 (0.2 g) in dry acetonitrile (7 ml) under a nitrogen atmosphere. The mixture was stirred at 23° for 30 min, then diluted with dichloromethane (20 ml) and washed with brine (20 ml). The organic solution was dried, concentrated in vacuo and the residue was triturated with diethyl ether to give the title compound as a white solid (0.221 g). M.p. 263°–5°. T.l.c. CH-EA (1:1), Rf 0.52. IR: 3300 (NH), 1717 and 1674 (C=O) cm–1; 1H-NMR: 7.48 (dd); 7.45–7.24 (m); 7.19–7.10 (m): 6.98 (dd); 6.93 (dd); 6.61 (s); 6.58–6.45 (m); 6.38 (d); 5.29 (d); 4.49–3.37 (m); 2.92 (s); 1.87 (m); 1.63–1.53 (m); 1.44–1.34 (m).

EXAMPLE 43

N-[1-(1-Adamantylmethyl)-2,4-dioxo-5-phenyl-2,3,4,5-tetrahydro-1H-1,5-benzodiazepin-3-yl]-N'-(3-carboxyphenyl)urea An aqueous 0.1M solution of lithium hydroxide (6.6 ml) was added to a solution of Example 41 (0.2 g) in THF (15 ml) previously cooled to 0°. The solution was stirred at 23°, for 16 h, then heated to 60° for 1 h and to 80° for 13 h. The solution was cooled to 23°, neutralized with acetic acid, concentrated in vacuo and the residue purified by flash chromatography (eluting in gradient from CH-EA 3:1 to DCM and finally to DCM-MeOH 10:1) to give the title compound as a white solid (0.183 g), still containing traces of inorganic salts. A sample was further purified by dissolution in DCM and washing with 10% hydrochloric acid; the organic layer was dried, concentrated in vacuo and the residue triturated with diethyl ether to give the pure title compound. M.p. 260°–70° (dec). T.l.c. EA, Rf 0.64. IR: 3354 (NH and OH),m 1701 and 1684 (C=O) cm–1; 1H-NMR: 9.21(s); 7.9–7.8(m); 7.6–7.16(m); 7.0–6.9(m); 4.99(d); 4.30(d); 3.60(d); 1.83(s); 1.65–1.2(m).

EXAMPLE 44

N-[1-(Adamantanmethyl)-2,4-dioxo-7-fluoro-5(4-fluorophenyl)-2,3,4,5-tetrahydro-1H-1,5benzodiazepin-3-yl]-N'(3-dimethylamino)phenylurea A solution of 3-Dimethylaminophenyl isocyante (0.043 g) in dry acetonitrile (3 ml) was added to a solution of the intermediate 95 (0.079 g) in dry acetonitrile (5 ml) under a nitrogen to a solution of the mixture was stirred at 23 C. for 1 h diluted with DCM, washed with brine (30 ml), evaporated to give the crude compound (0.145 g) which was triturated with ethyl ether to give the title compound as a white solid (0.046 g) M.p. >270. T.l.c. CH-EA (1:1), Rf 0.61. IR: 3439, 3333(NH); 1715 (C=O), 1610 and 1590 (C=C) cm–1; 1H-NMR: 7.46(dd); 7.38–7.3(m)1 7.20–7.10(m); 7.06–7.00(m); 6.78(t); 6.69–6.58(m); 6.49(dd); 6.27(d); 5.26(d); 4.49(d); 3.28(d); 2.93(s); 1.88(bs); 1.67–1.30(m).

EXAMPLE 45

(+)-N-[1-(Adamantanmethyl)-2,4-dioxo-5-phenyl-2,3,4,5-tetrahydro-1H-1,5-benzodiazepin-3-yl]-N'-phenylurea Phenyl isocyante (0.033 ml) was added to a solution of intermediate 97 (0.096 g) in dry acetonitrile (9 ml). The mixture was stirred at 23° under a nitrogen atmosphere for 1 h, then it was diluted with dichloromethane (40 ml) and washed with brine (2×20 ml). The organic layer was dried and concentrated in vacuo. Crystallisation of the crude material from ethyl acetate afforded the title compound (0.075 g) as white needles. M.P. 264°–5°. T.l.c. CH-EA (50:50), Rf 0.77 [alpha]$_D$=+38.4. IR (nujol): 3400(NH); 1707 and 1653 (C=O), 1597 and 1551 (C=C) cm$^{-1}$. 1H-NMR: 7.48(d); 7.46–7.20(m); 7.16(m); 7.04–6.94(m); 6.92(s); 6.37(d); 5.29(d); 4.48(d); 3.38(d); 1.85(m); 1.64–1.30(m).

EXAMPLE 46

(+) N-[1-(Adamantylmethyl)-2,4-dioxo-5-phenyl-2,3,4,5-tetrahydro-1H-1,5-benzodiazepin-3-yl]-N'-(3-ethoxycarbonylphenyl)urea 3-Ethoxycarbonylphenyl isocyante (0.152 ml) was added to a solution of intermediate 97 (0.490 g) in dry acetonitrile (20 ml) under a nitrogen atmosphere. The mixture was stirred at 23° for 1 h, then diluted with dichloromethane (20 ml) concentrated under vacuum and the residue was triturated with diethyl ether to give the title compound as a white solid (0.543 g). M.p. 220°–1°. [alpha]$_D$=+60.8, (CHCl$_3$, c=1.020) T.l.c. CH-EA (2:1), Rf 0.35. IR: 1709, 1670 and 1690 (C=O) cm$^{-1}$; 1H-NMR: 7.93(t); 7.64(m); 7.44–7.39(m); 7.35–7.27(m); 7.24–7.14(m); 7.38(bs); 6.89(dd); 6.58(d); 5.31(d); 4.50(d); 4.34(q); 3.38(d); 1.85(m); 1.61(m); 1.51(m); 1.45(m); 1.37(m); 1.35(t).

EXAMPLE 47

(+)N-[1-(1-Adamantylmethyl)-2,4-dioxo-5-phenyl-2,3,4,5-tetrahydro-1H-1,5benzodiazepin-3-yl]-N'(3-carboxyphenyl)urea Aluminium iodide (0.137 g) was added to a suspension of Example 46 (0.10 g) in dry acetonitrile (10 ml). The reaction mixture was stirred 6 h at 80° then cooled to 23°, dilute with dichloromethane (30 ml) and poured into ice (10 g). The aqueous layer was acidified with a 10% solution of hydrochloric acid (1 ml), washed with 5% solution of sodium thiosulphate (20 ml) and extracted with dichloromethane (2×25 ml). The collected organic phases were washed with water (30 ml) and brine (10 ml) dried and evaporated to give a white solid (0.118 g). This material was purified on silica gel, eluted with CH/EA 1/1 and then EA/Methanol 1/1 to give the title compound (41mg). T.l.c. EA, Rf 0.64. IR: 3354 (NH and OH), 1701 and 1684 (C=O) cm$^{-1}$; $^1$H-NMR: 9.21(s); 7.9–7.8(m); 7.6–7.16(m); 7.0–6.9(m); 4.99(d); 4.30(d); 3.60(d); 1.83(s); 1.65–1.2(m).

EXAMPLE 48

N-[2,4-dioxo-7-fluoro-1-(3-methylbut-1-yl)-5-phenyl-2,3,4,5-tetrahydro-1H-1,5-benzodiazepin-3-yl]N'-(3-dimethylamino)phenylurea 3-Dimethylaminophenyl isocyante (0.055 g) was added to a solution of the intermediate 100 (0.08 g) in dry acetonitrile (5 ml) under a nitrogen atmosphere. The mixture was stirred at 23° for 30 min.; the obtained precipitate was filtered and washed with ethyl ether to give the title compound as a white solid (0.086 g). M.p. 249–51°. T.l.c: CH-EA (1:1), Rf 0.5. IR: 1705, 1672 and 1636 (C=O), 1607 (C=C) cm$^{-1}$; $^1$H-NMR: 7.0–7.50(m); 6.81(bt); 6.68(dd); 6.62–6.46(dd); 6.51(bs); 6.28(d); 5.31(d); 4.54–3.60(m); 2.92 (s); 1.6–1.40(m); 0.95–0.85(d).

Pharmacy Example

| Capsules or Tablets | mg/dosage form |
|---|---|
| Active ingredient | 0.1 |
| Polyethyleneglycol | 15.0 |
| Lactose | 52.4 |
| Starch | 30.0 |
| Magnesium stearate | 0.5 |
| Silicon dioxide | 1.0 |
| Sodium Lauryl Sulphate | 1.0 |
|  | 100.0 |

The active ingredient is dispersed in a suitable solvent (e.g. ethanol) together with polyethyleneglycol. The solvent is removed. The powder so obtained is blended with the other excipients. The blend can be used to fill gelatine capsules or compressed using appropriate punches. The tablets can be coated using conventional techniques and coatings.

| Active ingredient | 0.1 |
|---|---|
| Povidone | 15.4 |
| Lactose | 74.0 |
| Hydrogenated vegetable oils | 3.0 |
| Silicon dioxide | 1.0 |
| Sodium Laauryl sulphate | 1.5 |
| Crospovidone | 5.0 |
|  | 100.0 |

The active ingredient is dispersed in a suitable solvent (e.g. ethanol) together with povidone. The solution is sprayed on to lactose and the solvent removed. The powder obtained is blended with the other excipients. The blend is used to fill gelatine capsules or compressed using appropriate punches. The tablet can be coated using conventional techniques and coatings.

| Oral liquid | |
|---|---|
| Active ingredient | 70–100 micrograms/dose |
| ethanol | 5–15% |
| Sodium saccharinate | 0.1–1% |
| Propylene glycol | q.b. 100% |
| Injection Formulation | |
| Active ingredient | 0.1–100 microgramms |
| Sodium phosphate | 1.50 mg/ml |
| NaOH | qs desired pH (range 3–9) |
| glyerol | 10–500 mg/ml |
| water for injection | qs to 0.5–10 ml |

Pack in glass (ampules) with a rubber stopper (vials, syringes) and a plastic/metal overseal (vials only). An inert gas atmosphere (for example nitrogen) may be introduced into dead space of container.

CCK—Antagonist Activity

The CCK-A antagonist and CCK-B antagonist activities of compounds of the invention were determined using the guinea pig isolated ileum longitudinal muscle myenteric plexus preparation. The compounds were tested using the procedure G Dal Forno et al J. Pharmacol. Exp & Ther. 261–1056–1063 1992 and the pKb value for each compound was determined.

The results obtained with representative compounds of the invention were as follows:

|  | pKb | |
|---|---|---|
| Compounds of Ex No. | CCK-A | CCK-B |
| 4 | 5.5 | 10.1 |
| 14 | 6.8 | 8.5 |
| 25 | <6.0 | 9.1 |
| 26 | ≦5.5 | 8.7 |
| 45 | 5.9 | 8.9 |

CCK—Receptor Binding

The binding affinity of the compounds of the invention for the CCK-A receptor (Pancreas Assay) and CCK-B receptor (guinea pig cortex assay) was determined using the procedure of G Dal Forno et al J. Pharmacol. Exp & Ther. 261–1056–1063. The pKi values determined with representative compounds of invention were as follows:

|  | pKi | |
|---|---|---|
| Compound Ex No | CCK-A | CCK-B |
| 4 | 6.9 | 9.6 |
| 7A | 6.33 | 8.71 |
| 9 | 6.02 | 8.31 |
| 11 | 5.80 | 8.01 |
| 14 | 6.15 | 8.64 |
| 16 | 6.95 | 9.17 |
| 25 | 6.49 | 8.81 |
| 26 | 6.30 | 8.81 |
| 27 | 6.83 | 9.54 |
| 30 | 7.00 | 9.14 |
| 31 | 6.76 | 8.82 |
| 39 | 6.52 | 8.72 |
| 41 | 6.09 | 8.53 |
| 45 | 5.95 | 9.02 |

The compounds of the invention are essentially non-toxic and therapeutically useful doses. Thus fore example no untoward effects were observed when the compound of Example 45 was given orally to mice and rats at doses at which the compound exhibits anxiolytic activity.

We claim:
1. A compound of formula (I)

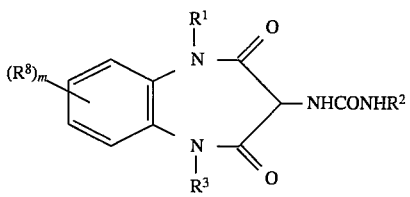

wherein
- $R^1$ represents a phenyl, $C_{3-7}$cycloalkyl, $C_{7-11}$bridgedcycloalkyl or $C_{1-6}$alkyl group which alkyl group may be substituted by a hydroxy, phenyl, $C_{1-6}$alkoxycarbonyl, $C_{3-7}$cycloalkyl, or $C_{7-11}$ bridgedcycloalkyl group;
- $R^2$ represents a substituted or unsubstituted phenyl group (wherein the substituents may be 1 or 2 of halo, $C_{1-4}$alkyl, nitro, cyano, trifluoromethyl, trifluoromethoxy, $C_{1-4}$alkylthio or $(CH_2)_n R^4$ wherein $R^4$ is hydroxy, $C_{1-4}$alkoxy, $CO_2 R^5$ or $NR^6 R^7$;
- $R^3$ is phenyl optionally substituted by one or two halogen atoms;
- $R^5$ represents hydrogen or a $C_{1-4}$alkyl group;
- $R^6$ and $R^7$ independently represent hydrogen or a $C_{1-4}$alkyl group;
- $R^8$ represents hydrogen or a halogen atom; m is zero, 1 or 2;
- n is zero or 1; and pharmaceutically acceptable salts and solvates thereof.

2. A compound as claimed in claim 1 wherein $R^1$ represents phenyl, phenethyl, bridged $C_{7-10}$cycloalkyl, $C_{4-6}$alkyl, $C_{3-6}$hydroxyalkyl, $C_{1-2}$alkyl substituted by bridged $C_{7-10}$cycloalkyl, alkoxycarbonylmethyl or $C_{2-3}$alkyl substituted by $C_{3-7}$cycloalkyl.

3. A compound as claimed in claim 1 wherein $R^1$ represents 3-methylbutyl, 3,3-dimethylbutyl, 2hydroxy-3-methylbutyl, 2-hydroxy-3,3-dimethylbutyl, 2-cyclopentylethyl, 5-norbornenylmethyl or 1-adamantylmethyl.

4. A compound as claimed in claim 1 wherein $R^2$ represents phenyl optionally substituted by bromine, clorine, fluorine, methyl, methoxy, methylthio, trifluoromethoxy, cyano, dimethylamino, or $(CH_2)_n CO_2 R^5$ wherein $R^5$ is hydrogen or $C_{1-4}$alkyl.

5. A compound as claimed in claim 1 wherein $R^2$ represents phenyl optionally substituted by methoxy, cyano, nitro, methylthio, dimethylamino, ethoxycarbonyl or carboxyl.

6. A compound as claimed in claim 1 wherein $R^3$ represents phenyl optionally substituted by fluorine in ortho or para position.

7. A compound as claimed in claim 1 wherein $R^8$ represents hydrogen, chlorine or fluorine.

8. A compound as claimed in claim 1 having the configuration

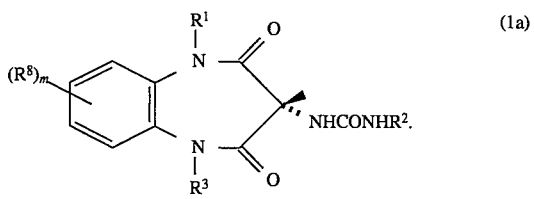

9. N-phenyl-N'-[2,3,4,5-tetrahydro-2,4-dioxo-1-(1-adamantylmethyl)-5-phenyl-1H-1,5-phenyl-1H-1,5-benzodiazepin-3-yl]urea and the (+) enantiomer thereof and salts thereof.

10. N[1-(1-Adamantylmethyl)-2,4-dioxo-5-phenyl-2,3,4,5-tetrahydro-1H-1,5-benzodiazepin-3-yl]-N'-(3-carboxyphenyl)urea
N-phenyl-N'-[2,3,4,5-tetrahydro-2,4-dioxo-1-(3-methylbutyl)-5-phenyl-1H-1,5-benzodiazepin-3-yl]urea;
N-(3-dimethylaminophenyl)-N'-[2,3,4,5,-tetrahydro-2,4-dioxo-1-(3-methylbutyl)-5-(2-fluorophenyl)-1H-1,5-benzodiazepin-3-yl]urea;
and the (+) enantiomers thereof and salts thereof.

11. Pharmaceutical compositions comprising an effective amount of a compound as claimed in claim 1 in admixture with one or more physiologically acceptable carriers or excipients.

12. A method of treatment of a mammal including man for conditions where modification of the effects of gastrin and or CCK is a therapeutic benefit comprising administration of an effective amount of a compound as claimed in claim 1.

13. A pharmaceutical composition comprising an effective amount of a compound as claimed in claim 9 in admixture with one or more physiological acceptable carriers or excipients.

14. A method of treatment of a mammal including man for conditions where modification of the effects of gastrin and/or CCK is a therapeutic benefit comprising administration of an effective amount of a compound as claimed in claim 9.

* * * * *